US012799180B2

(12) United States Patent
Russell et al.

(10) Patent No.: US 12,799,180 B2
(45) **Date of Patent: *Nov. 17, 2026**

(54) VESICULAR STOMATITIS VIRUSES

(71) Applicant: Mayo Foundation for Medical Education and Research, Rochester, MN (US)

(72) Inventors: Stephen James Russell, Rochester, MN (US); Shruthi Naik, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 897 days.

This patent is subject to a terminal disclaimer.

(21) Appl. No.: 18/120,798

(22) Filed: Mar. 13, 2023

(65) Prior Publication Data

US 2024/0083966 A1 Mar. 14, 2024

Related U.S. Application Data

(60) Continuation of application No. 16/916,482, filed on Jun. 30, 2020, now Pat. No. 11,634,469, which is a continuation of application No. 15/925,279, filed on Mar. 19, 2018, now Pat. No. 10,752,666, which is a continuation of application No. 15/246,189, filed on Aug. 24, 2016, now Pat. No. 9,951,117, which is a division of application No. 13/820,453, filed as application No. PCT/US2011/050227 on Sep. 1, 2011, now Pat. No. 9,428,736.

(60) Provisional application No. 61/379,644, filed on Sep. 2, 2010.

(51) Int. Cl.

| | |
|---|---|
| ***C07K 14/705*** | (2006.01) |
| ***A61K 35/766*** | (2015.01) |
| ***A61K 38/21*** | (2006.01) |
| ***A61K 48/00*** | (2006.01) |
| ***C07K 14/565*** | (2006.01) |

(52) U.S. Cl.

CPC .......... *C07K 14/705* (2013.01); *A61K 35/766* (2013.01); *A61K 38/215* (2013.01); *A61K 48/005* (2013.01); *C07K 14/565* (2013.01); *C12N 2760/20232* (2013.01); *C12N 2760/20243* (2013.01)

(58) Field of Classification Search

None

See application file for complete search history.

(56) References Cited

U.S. PATENT DOCUMENTS

| | | | |
|---|---|---|---|
| 4,108,983 | A | 8/1978 | Wallack |
| 4,500,512 | A | 2/1985 | Barme |
| 4,985,244 | A | 1/1991 | Makino et al. |
| 5,001,692 | A | 3/1991 | Farla et al. |
| 5,137,727 | A | 8/1992 | Eckenhoff |
| 5,262,359 | A | 11/1993 | Hierholzer |
| 5,304,367 | A | 4/1994 | Biegon |
| 5,631,237 | A | 5/1997 | Dzau et al. |
| 5,661,032 | A | 8/1997 | Miller et al. |
| 5,703,056 | A | 12/1997 | Blasberg |
| 5,713,858 | A | 2/1998 | Heruth et al. |
| 5,738,985 | A | 4/1998 | Miles et al. |
| 5,980,508 | A | 11/1999 | Cardamone et al. |
| 6,012,034 | A | 1/2000 | Hamparian et al. |
| 6,026,316 | A | 2/2000 | Kucharczyk et al. |
| 6,083,751 | A | 7/2000 | Feldhaus et al. |
| 6,095,976 | A | 8/2000 | Nachtomy et al. |
| 6,110,461 | A | 8/2000 | Lee et al. |
| 6,358,683 | B1 | 3/2002 | Collins |
| 6,391,579 | B1 | 5/2002 | Carrasco et al. |
| 6,428,968 | B1 | 8/2002 | Molnar-Kimber et al. |
| 6,440,419 | B1 | 8/2002 | Hein et al. |
| 6,586,411 | B1 | 7/2003 | Russell |
| 6,632,800 | B1 | 10/2003 | Russell |
| 6,821,725 | B1 | 11/2004 | Carrasco et al. |
| 7,645,865 | B2 | 1/2010 | Russell |
| 7,982,022 | B2 | 7/2011 | Russell |
| 9,428,736 | B2 | 8/2016 | Russell et al. |
| 9,951,117 | B2 | 4/2018 | Russell et al. |
| 10,752,666 | B2 | 8/2020 | Russell et al. |
| 11,634,469 | B2 | 4/2023 | Russell et al. |
| 2002/0042127 | A1 | 4/2002 | Russell |
| 2003/0044386 | A1 | 3/2003 | Barber |

(Continued)

FOREIGN PATENT DOCUMENTS

| | | |
|---|---|---|
| EP | 0700995 | 3/1996 |
| JP | 2004-525855 | 8/2004 |

(Continued)

OTHER PUBLICATIONS

Wang et al. 564. Personalized Approach to Determine Susceptiblity to Replicating Oncolytic Vector Expressing IFNb: Heterogeneity in IFN-Responsiveness Defines Efficacy. Molecular Therapy, 2009. 17(1), S215-S216.*

Abai et al., "Insulin Delivery with Plasmid DNA," Human Gene Ther., 1999, 10:2637-2649.

Aggarwal et al., "Models for Prevention and Treatment of Cancer: Problems vs. Promises," Biochemical Pharmacology., 78(9):1083-1094, Nov. 1, 2009.

Albonico et al., "Febrile infectious childhood diseases in the history of cancer patients and matched controls," Medical Hypotheses, 1998, 51:315-320.

Alemany et al., "Replicative adenoviruses for cancer therapy," Nature Biotechnology, 2000, 18:723-727.

(Continued)

*Primary Examiner* — Christopher M Babic
*Assistant Examiner* — Kimberly A Aron
(74) *Attorney, Agent, or Firm* — Fish & Richardson P.C.

(57) ABSTRACT

This document provides methods and materials related to vesicular stomatitis viruses. For example, vesicular stomatitis viruses, nucleic acid molecules encoding VSV polypeptides, methods for making vesicular stomatitis viruses, and methods for using vesicular stomatitis viruses to treat cancer are provided.

4 Claims, 12 Drawing Sheets

Specification includes a Sequence Listing.

(56) References Cited

U.S. PATENT DOCUMENTS

| | | | |
|---|---|---|---|
| 2003/0091592 | A1 | 5/2003 | Barber |
| 2003/0118553 | A1 | 6/2003 | Petrich et al. |
| 2004/0209830 | A1 | 10/2004 | Russell |
| 2006/0127981 | A1 | 6/2006 | Bergman et al. |
| 2007/0092968 | A1 | 4/2007 | Ji et al. |
| 2010/0330197 | A1 | 12/2010 | Higashiguchi |
| 2011/0015239 | A1 | 1/2011 | Verkman et al. |
| 2012/0027676 | A1 | 2/2012 | Ho et al. |
| 2013/0251681 | A1 | 9/2013 | Russell et al. |
| 2014/0271456 | A1 | 9/2014 | Russell |
| 2016/0046680 | A1 | 2/2016 | Russell |
| 2017/0051255 | A1 | 2/2017 | Russell et al. |
| 2018/0237492 | A1 | 8/2018 | Russell et al. |
| 2020/0325204 | A1 | 10/2020 | Russell |

FOREIGN PATENT DOCUMENTS

| | | |
|---|---|---|
| WO | WO 1997/012032 | 4/1997 |
| WO | WO 1997/012048 | 4/1997 |
| WO | WO 1998/045443 | 10/1998 |
| WO | WO 1999/060135 | 11/1999 |
| WO | WO 2000/076450 | 12/2000 |
| WO | WO 2001/013106 | 2/2001 |
| WO | WO 2001/019380 | 3/2001 |
| WO | WO 2011/133216 | 10/2011 |
| WO | WO 2012/031137 | 3/2012 |

OTHER PUBLICATIONS

Alvarez-Breckenridge et al., "Pharmacologic and Chemical Adjuvants in Tumor Virotherapy," Chemical Reviews, vol. 109(7), Jul. 2009, pp. 3125-3140.

Anderson, "Human gene therapy," Nature, 1998, 392(Supp.):25-30.

Andreansky et al., "The application of genetically engineered herpes simplex viruses to the treatment of experimental brain tumors," Proc. Natl. Acad. Sci. USA, 1996, 93:11313-11318.

Appelros et al., "Activation peptide of carboxypeptidase B in serum and urine in acute pancreatitis," Gut, 1998, 42:97-102.

Arbit et al., "Quantitative studies of monoclonal antibody targeting to disialoganglioside GD2 in human brain tumors," Eur. J. Nucl. Med., 1995, 22:419-426.

Asada, "Treatment of Human Cancer with Mumps Virus," Cancer, 1974, 34:1907-1928.

Aversa et al., "An interleukin 4 (IL-4) mutant protein inhibits both IL-4 or IL-13-induced human immunoglobulin G4 (IgG4) and IgE synthesis and B cell proliferation: support for a common component shared by IL-4 and IL-13 receptors," J Exp Med., 178(6):2213-2218, Dec. 1, 1993.

Bae et al., "Genomic Differences between the Diabetogenic and Nondiabetogenic Vairants of Encephalomyocarditis Virus," Virology, 1989, 170:282-287.

Basu et al., "Inhibition of vesicular stomatitis virus infection in epithelial cells by alpha interferoninduced soluble secreted proteins," J Gen Virol., 87(Pt 9):2653-2662, Sep. 2006.

Bateman et al., "Fusogenic Membrane Glycoproteins—A Novel Class of Cytotoxic Genes with Immunostimulatory Properties," Gene Therapy, 1999, 6(Suppl. 1):S6, Abstract #24.

Bateman et al., "Fusogenic membrane glycoproteins as a novel class of genes for the local and immune-mediated control of tumor growth," Cancer Res., 2000, 60:1492-1497.

Belkowski and Sen, "Inhibition of vesicular stomatitis viral mRNA synthesis by interferons," J. Virol., 61(3):653-660, Mar. 1987.

Bennett et al., "Fusion of Green Fluorescent Protein with the Zeocin™-Resistance Marker Allows Visual Screening and Drug Selection of Transfected Eukaryotic Cells," BioTechniques, 1998, 24(3):478-482.

Berg et al., "Physiological functions of endosomal proteolysis," Biochem. J., 1995, 307:313-326.

Bluming and Ziegler, "Regression of Burkitt's Lymphoma in Association with Measles Infection," Lancet, 1971, pp. 105-106.

Bolt and Pedersent, "The Role of Subtilisin-like Proprotein Convertases for Cleavage of the Measles Virus Fusion Glycoprotein in Different Cell Types," Virology, 1998, 252:387-398.

Brandenburg, "History and Diagnostic Significance of C-Peptide," Experimental Diabetes Research, vol. 2008, Article ID 576862, 7 pages, 2008.

Buchholz et al., "In vivo selection of protease cleavage sites from retrovirus display libraries," Nat Biotechnol., 16(10):951-954, Oct. 1998.

Cathomen et al., "A matrix-less measles virus is infectious and elicits extensive cell fusion: consequences for propagation in the brain," EMBO J., 1998, 17(14):3899-3908.

Cathomen et al., "Measles Viruses with Altered Envelope Protein Cytoplasmic Tails Gain Cell Fusion Competence," J. Virol., 1998, 72(2):1224-1234.

Ch'ien et al., "Fatal subacute immunosuppressive measles encephalitis (SIME) in children with acute lymphocytic leukemia—clinical, electroencephalographic, and computerized tomographic scan features," Clin. Electroencephalogr., 1983, 14(4):214-220.

Chambers et al., "Comparison of genetically engineered herpes simplex viruses for the treatment of brain tumors in a scid mouse model of human malignant glioma," Proc. Natl. Acad. Sci. USA, 1995, 92:1411-1415.

Cianchetta et al., "Perchlorate transport and inhibition of the sodium iodide symporter measured with the yellow fluorescent protein variant YFP-H148Q/1152L," Toxicol Appl Pharmacol., 243(3):372-380, Epub Dec. 18, 2009.

Cleutjens, K.B.J.M. et al., "A 6-kb promoter fragment mimics in transgenic mice the prostatespecific and androgen-regulated expression of the endogenous prostate-specific antigen gene in humans," Molecular Endocrinology, 1997, 11:1256-1265.

Cohen et al., "Complete nucleotide sequence of an attenuated hepatitis A virus: Comparison with wild-type virus," Proc. Natl. Acad. Sci. USA, 1987, 84:2497-2501.

Communication on Reexamination App. No. 201180050698.2, dated Sep. 30, 2016, 9 pages with English Translation.

Conzelmann, "Nonsegmented negative-strand RNA viruses: genetics and manipulation of viral genomes," Annu Rev Genet., 32:123-162, 1998.

Costello et al., "Evidence for Changes in RREB-1, ZIP3, and Zinc In the Early Development of Pancreatic Adenocarcinoma," J Gastrointest Cancer., 43(4):570-578, Dec. 2012.

Crawford et al., "Thyroid vol. measurement in thyrotoxic patients: comparison between ultrasonography and iodine-124 positron emission tomography," Eur. J. Nucl. Med., 1997, 24:1470-1478.

D'agostino et al., "IFN-beta-induced alteration of VSV protein phosphorylation in neuronal cells," Viral Immunol., 22(6):353-369, Dec. 2009.

Dai et al., "Cloning and characterization of the thyroid iodide transporter," Nature, 1996, 379:458-460.

De Felipe et al., "Use of the 2A sequence from foot-and-mouth disease virus in the generation of retroviral vectors for gene therapy," Gene Therapy, 1999, 6:198-208.

De Swart et al., "Measles in a Dutch hospital introduced by an immuno-compromised infant from Indonesia infected with a new virus genotype," Lancet, 2000, 355:201-202.

Delassus et al., "Genetic Organization of Gibbon Ape Leukemia Virus," Virology, 1989, 173:205-213.

Di Bernardo et al., "Intracellular anion fluorescence assay for sodium/iodide symporter substrates," Analytical Biochemistry, vol. 415(1), Aug. 2011, pp. 32-38.

Dingli et al., "In vivo imaging and tumor therapy with the sodium iodide symporter," Journal of Cellular Biochemistry, vol. 90(6), Dec. 2003, pp. 1079-1086.

Douglass et al., "Polyprotein Gene Expression: Generation of Diversity of Neuroendocrine Peptides," Ann. Rev. Biochem., 1984, 53:665-715.

Duechler et al., "Evolutionary relationships within the human rhinovirus genus: comparison of serotypes 89, 2, and 14," Proc Natl Acad Sci U S A., 84(9):2605-2609, May 1987.

Duprex et al., "Observation of Measles Virus Cell-to-Cell Spread in Astrocytoma Cells by Using a Green Fluorescent Protein-Expressing Recombinant Virus," J. Virol., 1999, 73(11):9568-9575.

(56) References Cited

OTHER PUBLICATIONS

Earle et al., "The Complete Nucleotide Sequence of a Bovine Enterovirus," J. Gen. Virol., 1988, 69:253-263.
Eiselein et al., "Treatment of Transplanted Murine Tumors with an Oncolytic Virus and Cyclophosphamide," Cancer Res., 1978, 38:3817-3822.
Endres et al., "Measurement of parathyroid hormone," Endocrinol Metab Clin North Am., 18(3):611-629, Sep. 1989.
European Search Report for Application No. EP11822676.0, mailed Jan. 31, 2014, 4 pages.
Evermann and Burnstein, "Immune Enhancement of the Tumorigenicity of Hamster Brain Tumor Cells Persistently Infected with Measles Virus," Int. J. Cancer, 1975, 16:861-869.
Faham et al., "The crystal structure of a sodium galactose transporter reveals mechanistic insights into Na+/sugar symport," Science, 321(5890):810-814, Epub Jul. 3, 2008.
Flower et al., "Dose-response study on thyrotoxic patients undergoing positron emission tomography and radioiodine therapy," Eur. J. Nucl. Med., 1994, 21:531-536.
Flower et al., "Thyroid imaging using position emission tomography—a comparison with ultrasound imaging and conventional scintigraphy in thyrotoxicosis," Br. J. Radiol., 1990, 63:325-330.
Galanis et al., "Use of Fusogenic Membrane Glycroproteins as Novel Therapeutic Transgenes in Gliomas," Gene Therapy, 1999, 6(S1):S7, Abstract #28.
Gambhir et al., "Assays for Noninvasive Imaging of Reporter Gene Expression," Nucl. Med. Biol., 1999, 26:481-490.
Gardella et al., "Expression of Human Parathyroid Hormone-(1-84) in Escherichia coli as a Factor X-cleavable Fusion Protein," The Journal of Biological Chemistry, vol. 265(26), Sep. 1990, pp. 15854-15859.
GenBank® Accession No. AF235001.1, GI No. 12642413, "Mus musculus sodium iodide symporter NIS mRNA, complete cds," Feb. 1, 2001, 2 pp.
GenBank® Accession No. AF380353.1, GI No. 14290144, "Mus musculus sodium iodide symporter mRNA, complete cds," Jun. 5, 2001, 2 pp.
GenBank® Accession No. BC105047.1, GI No. 85397519, "*Homo sapiens* solute carrier family 5 (sodium iodide symporter), member 5, mRNA (cDNA clone MGC:132707 Image:8144050), complete cds," Jul. 21, 2006, 3 pp.
GenBank® Accession No. BC105049.1, GI No. 85397913, "*Homo sapiens* solute carrier family 5 (sodium iodide symporter), member 5, mRNA (cDNA clone MGC:132709 Image:8144052), complete cds," Jul. 21, 2006, 3 pp.
GenBank® Accession No. BC119395.1, GI No. 111601321, "Mus musculus interferon beta 1, fibroblast, mRNA (cDNA clone MGC:155711 Image:8734144), complete cds," Aug. 9, 2006, 2 pp.
GenBank® Accession No. BC119397.1, GI No. 111601034, "Mus musculus interferon beta 1, fibroblast, mRNA (cDNA clone MGC:155713 Image:8734146), complete cds," Aug. 9, 2006, 2 pp.
GenBank® Accession No. NC_001560, GI No. 9627229, "Vesicular stomatitis Indiana virus, complete genome," Apr. 29, 2010, 8 pp.
GenBank® Accession No. NM_000453.2, GI No. 164663746, "*Homo sapiens* solute carrier family 5 (sodium iodide symporter), member 5 (SLC5A5), mRNA," Aug. 2, 2010, 5 pp.
GenBank® Accession No. NM_002176.2, GI No. 50593016, "Homo sapiens interferon, beta 1, fibroblast (IFNB1), mRNA," Aug. 15, 2010, 3 pp.
GenBank® Accession No. NM_010510.1, GI No. 6754303, "Mus musculus interferon beta 1, fibroblast (Ifnb1), mRNA," Jun. 20, 2010, 3 pp.
GenBank® Accession No. NM_019127.1, GI No. 9506800, "Rattus norvegicus interferon beta 1, fibroblast (Ifnb1), mRNA," Feb. 7, 2010, 2 pp.
GenBank® Accession No. NM_052983.2, GI No. 158138504, "Rattus norvegicus solute carrier family 5 (sodium iodide symporter), member 5 (Slc5a5), mRNA," Jun. 6, 2010, 3 pp.
GenBank® Accession No. NM_053248.2, GI No. 162138896, "Mus musculus solute carrier family 5 (sodium iodide symporter), member 5 (Slc5a5), mRNA," Mary 6, 2010, 4 pp.
GenBank® Accession No. NM_214410, GI No. 47523871, "Sus scrofa solute carrier family 5 (sodium iodide symporter), member 5 (SLC5A5), mRNA," May 29, 2010, 2 pp.
GenBank® Accession No. U60282, GI No. 1399953, "Rattus norvegicus thyroid sodium/iodide symporter NIS mRNA, complete cds," Jul. 2, 1996, 2 pp.
GenBank® Accession No. XM 524154, GI No. 114676080, "Predicted: Pan troglodytes solute carrier family 5 (sodium iodide symporter), member 5 (SLC5A5), mRNA," Sep. 16, 2006, 2 pp.
GenBank® Accession No. XM 541946, GI No. 73986161, "Predicted: Canis familiaris similar to Sodium/iodide cotransporter (Na(+)/I(−) cotransporter) (Sodium-iodide symporter) (Na(+)/I(−)-symporter) (LOC484830), mRNA," Aug. 30, 2005, 2 pp.
GenBank® Accession No. XM 581578, GI No. 297466916, "Predicted: Bos taurus solute carrier family 5 (sodium iodide symporter), member 5 (SLC5A5), mRNA," Jun. 3, 2010, 2 pp.
Giam et al., "In Vivo and In Vitro Autoprocessing of Human Immunodeficiency Virus Protease Expressed in *Escherichia coli*," The Journal of Biological Chemistry, vol. 263(29), Oct. 1988, pp. 14617-14620.
Goel et al., "Radioiodide imaging and radiovirotherapy of multiple myeloma using VSV(Delta51)-NIS, an attenuated vesicular stomatitis virus encoding the sodium iodide symporter gene," Blood, vol. 110(7), Oct. 2007, pp. 2342-2350.
Greentree, "Hodgkin's Disease: Therapeutic Role of Measles Vaccine," Am. J. Med., 1983, 75:928.
Gromeier et al., "Intergeneric poliovirus recombinants for the treatment of malignant glioma," Proc. Natl. Acad. Sci. USA, 2000, 97(12):6803-6808.
Grote et al., "Live attenuated measles virus induces regression of human lymphoma xenografts in immunodeficient mice," Blood, 2001, 97(12):3746-3754.
Gura, "Systems for Identifying New Drugs Are Often Faulty," Science, 1997, 278:1041-1042.
Hastie and Grdzelishvili., "Vesicular Stomatitis Virus As A Flexible Platform For Oncolytic Virotherapy Against Cancer," J Gen Virol., 93(Pt 12):2529-2545, 2012.
Hays et al., "A mathematical and physiological model for early distribution of radioiodide in man," Journal of Applied Physiology, vol. 20(6), Nov. 1965, pp. 1319-1328.
Henry et al., "A conserved asparagine residue in transmembrane segment 1 (TM1) of serotonin transporter dictates chloride-coupled neurotransmitter transport," J. Biol. Chem., 286(35):30823-30836, Epub Jul. 5, 2011.
Hilgert et al., "A monoclonal antibody applicable for determination of C-peptide of human proinsulin by RIA," Hybridoma, 10(3):379-386, Jun. 1991.
Hook, Proteolytic and Cellular Mechanisms in Prohormone and Proprotein Processing, Molecular Biology Intelligence Unit, 1998, R.G. Landes Company, Austin, Texas.
Hooper et al., "Membrane protein secretases," Biochem. J., 1997, 321:265-279.
Hughes et al., "The Complete Nucleotide Sequence of Coxsackievirus A21," J. Gen Virol., 1989, 70:2943-2952.
Hutton, "Insulin secretory granule biogenesis and the proinsulin-processing endopeptidases," Diabetologia, 1994, 37(Suppl. 2):S48-S56.
Iizuka et al., "Complete Nucleotide Sequence of the Genome of Coxsackievirus B1," Virology, 1987, 156:64-73.
Inchauspe et al., "Genomic structure of the human prototype strain H of hepatitis C virus: Comparison with American and Japanese isolates," Proc. Natl. Acad. Sci. USA, 1991, 88:10292-10296.
Institute of Physics, "Positron emission tomography," 2012. Dowloaded from the internet <https://www.iop.org/education/teacher/resources/teaching-medicalphysics/positron/file_56287.pdf> on Jan. 6, 2015, pp. 1-3.
International Preliminary Report on Patentability for PCT/US2011/050227, dated Mar. 5, 2013, 6 pages.
International Preliminary Report on Patentability for PCT/US2014/026120, mailed Sep. 24, 2015, 16 pages.

(56) References Cited

OTHER PUBLICATIONS

International Search Report and Written Opinion for PCT/US2011/050227, dated Apr. 18, 2012, 9 pages.
International Search Report and Written Opinion for PCT/US2014/26120, mailed Jan. 21, 2015, 27 pages.
Invitation to Pay Additional Fees for PCT/US2014/026120, mailed Nov. 13, 2014, 3 pages.
Iskandrian et al., "Automated assessment of serial SPECT myocardial perfusion images," Journal of Nuclear Cardiology, vol. 16(1), Feb. 2009, pp. 6-9.
Jackson, "Initiation without an end," Nature, 1991, 252(6339):14-15.
Jenkins et al., "The Complete Nucleotide Sequence of Coxsackievirus B4 and Its Comparison to Other Members of the Picornaviridae," J. Gen. Virol., 1987, 68:1835-1848.
Jenks et al., "Safety studies on intrahepatic or intratumoral injection of oncolytic vesicular stomatitis virus expressing interferon-beta in rodents and nonhuman primates," Hum Gene Ther., 21(4):451-462, Apr. 2010.
Johnson et al., "Baculovirus-insect cell production of bioactive choriogonadotropin-immunoglobulin G heavy-chain fusion proteins in sheep," Biol Reprod., 52(1):68-73, Jan. 1995.
Kao et al., "C-Peptide Immunochemiluminometric Assay Developed From Two Seemingly Identical Polyclonal Antisera," Ann. Clin. Lab. Sci., 1992, 22(5):307-316, 348-350.
Kato et al., "Molecular cloning of the human hepatitis C virus genome from Japanese patients with non-A, non-B hepatitis," Proc. Natl. Acad. Sci. USA, 1990, 87:9524-9528.
Kelly et al., "Attenuation of Vesicular Stomatitis Virus Encephalitis through MicroRNA Targeting," Journal of Virology, vol. 84(3), Feb. 2010, pp. 1550-1562.
Kenney and Pagano, "Viruses as Oncolytic Agents: a New Age for "Therapeutic" Viruses," J. Natl. Cancer Inst., 1994, 86(16):1185-1186.
Kimball, "The Fluorescence-Activated Cell Sorter," Kimball's Biology Pages [online] Feb. 2, 2011 [retrieved on Jan. 28, 2015]. Retrieved from the Internet: <URL: http://users.rcn.com/jkimball.ma.ultranet/BiologyPages/F/FACS.html>, 3 pages.
Kirn and McCormick, "Replicating viruses as selective cancer therapeutics," Mol. Med. Today, 1996, 2(12):519-527.
Kirn, "Replication-selective microbiological agents: fighting cancer with targeted germ warfare," J. Clin. Invest., 2000, 105(7):837-839.
Kirn, "Replication-selective oncolytic adenoviruses: virotherapy aimed at genetic targets in cancer," Oncogene, 2000, 19:6660-6669.
Kitabchi, "Proinsulin and C-peptide: a review," Metabolism, 26(5):547-587, May 1977.
Knapp et al., "Rhenium Radioisotopes for Therapeutic Radiopharmaceutical Development," International Seminar on Therapeutic Application of Radiophrmaceuticals (IAEA-SR-209), Hyderabad, India, Jan. 18-22, 1999, 5 pages.
Kuzumaki and Kobayashi, "Reduced Transplantability of Syngenic Mouse Tumors Superinfected with Membrane Viruses in NU/NU Mice," Transplantation, 1976, 22(6):545-550.
Lawson et al., "Recombinant vesicular stomatitis viruses from DNA," Proc Natl Acad Sci U S A, vol. 92(10), May 1995, pp. 4477-4481.
Lawson et al., "Recombinant vesicular stomatitis viruses from DNA," Proc Natl Acad Sci U S A, vol. 92(19), Sep. 1995, p. 9009.
Lech et al., "Study of radioisotope uptake and efflux in NIS expressing cells goes high-throughput," American society of gene and cell therapy (ASGT) 14th Annual Meeting, Abstract 538, Mol Ther., 19(1):S206, May 2011, 1 page.
Lichty et al., "Vesicular stomatitis virus: a potential therapeutic virus for the treatment of hematologic malignancy," Human Gene Therapy, vol. 15(9), Sep. 2004, pp. 821-831.
Linardakis et al., "Regulated Expression of Fusogenic Membrane Glycoproteins," Gene Therapy, 1999, 6(Suppl. 1):S4, Abstract #13.
Lorence et al., "Complete Regression of Human Neuroblastoma Xenografts in Athymic Mice After Local Newcastle Disease Virus Therapy," J. Natl. Cancer Inst., 1994, 86(16):1228-1233.
Lorence et al., "Newcastle Disease Virus as an Antineoplastic Agent: Induction of Tumor Necrosis Factor-α and Augmentation of Its Cytotoxicity," J. Nat. Cancer Inst., 1988, 80(16):1305-1312.
Lynch and Snyder, "Neuropeptides: Multiple Molecular Forms, Metabolic Pathways, and Receptors," Ann. Rev. Biochem., 1986, 55:773-799.
Macejak and Sarnow, "Internal initiation of translation mediated by the 5' leader of a cellular mRNA," Nature, 1991, 353:90-94.
Matzuk and Boime, "Mutagenesis and gene transfer define site-specific roles of the gonadotropin oligosaccharides," Biol Reprod., 40(1):48-53, Jan. 1989.
Mazzaferri, "Radioiodine and Other Treatments and Outcomes," The Thyroid—A Fundamental and Clinical Text, Braverman and Utiger (eds.), Seventh Edition, 1996, Lippincott—Raven Publishers, Philadelphia, pp. 922-945.
McInnes and Sykes, "Growth factor receptors: structure, mechanism, and drug discovery," Biopolymers., 43(5):339-366, 1997.
McMartin, "Molecular sieving, receptor processing and peptidolysis as major determinants of peptide pharmacokinetics in vivo," Biochem. Society Transactions, 1989, 17(5):931-934.
Megibow and Bosniak, "Dilute barium as a contrast agent for abdominal CT," AJR Am J Roentgenol., 134(6):1273-1274, Jun. 1980.
Mettler et al., "Virus Inoculation in Mice Bearing Ehrlich Ascitic Tumors: Antigen Production and Tumor Regression," Infection and Immunity, 1982, 37:23-27.
Mithöfer et al., "Quantitative Assay of Trypsinogen by Measurement of Cleaved Activation Peptide after Activation with Enterokinase," Analytical Biochem., 1995, 230:348-350.
Mitus et al., "Attenuated Measles Vaccine in Children with Acute Leukemia," Am. J. Dis. Children, 1962, 103:413-418.
Mota, "Infantile Hodgkin's Disease: Remission after Measles," Br. Med. J., 1973, 2:421.
Mullins and Mullins, "Molecular Medicine in Genetically Engineered Animals. Transgenesis in the Rat and Larger Mammals," J. Clin. Invest., 1996, 97(7):1557-1560.
Murakami and Etlinger, "Degradation of Proteins with Blocked Amino Groups by Cytoplasmic Proteases," Biochem. Biophys. Res. Comm., 1987, 146(3):1249-1255.
Nagasawa et al., "Changes of Plasma Levels of Human Growth Hormone with Age in Relation to Mammary Tumour Appearance in Whey Acidic Protein/Human Growth Hormone (mWAP/hGH) Transgenic Female and Male Mice," In Vivo, 1996, 10:503-506.
Naik et al., "Curative one-shot systemic virotherapy in murine myeloma," Leukemia, Aug. 2012, 26(8):1870-1878.
Naik et al., "Engineering VSV-IFN-NIS for the Treatment of Multiple Myeloma" Blood (ASH Annual Meeting Abstracts) Nov. 2009, vol. 114: Abstract 378, 1 page.
Naik et al., Engineering VSV-IFN-NIS for the treatment of Multiple Myeloma, Cold Spring Harbor Labs (CSHL), Barriers to In Vivo Delivery, Nov. 16-19, 2009, 1 page [abstract].
Naik et al., "High-resolution analysis of the intratumoral spread of an intravenously administered oncolytic virus" Mol. Ther., 18(1)S234-S235, May 2010, American Society of Gene and Cell Therapy (ASGCT) Annual conference May 19-22, 2010.
Naik et al., "Curative one-shot systemic virotherapy in murine myeloma," Leukemia, 26(8):1870-1878, Epub Mar. 19, 2012.
Naik et al., "Engineering oncolytic viruses to exploit tumor specific defects in innate immune signaling pathways," Expert Opinion on Biological Therapy, vol. 9(9), Sep. 2009, pp. 1163-1176.
Naik, "Oncolytic virotherapy for multiple myeloma," College of Medicine—Mayo Clinic, 2011, 184 pages.
Neagoe and Stolan, "Methods of Active Immunotherapy and Viral Oncolysis in some Forms of Cancer," Med Interne., 1986, 24(2):125-142.
Nemunaitis, "Oncolytic viruses," Investigational New Drugs, 1999, 17:375-386.
Neumann et al., "Preoperative 123-I/99mTc-Sestamibi Subtraction SPECT and SPECT/CT in Primary Hyperparathyroidism," The Journal of Nuclear Medicine, vol. 49(12), Dec. 2008, pp. 2012-2017.

(56) References Cited

OTHER PUBLICATIONS

Nies et al., "Principles of Therapeutics," In Goodman & Gilman's The Pharmacological Basis of Therapeutics, eds. Hardman, et al., McGraw-Hill, NY, 1996, pp. 43-62.
Obuchi et al., "Development of recombinant vesicular stomatitis viruses that exploit defects in host defense to augment specific oncolytic activity," J Virol., 77(16):8843-8856, Aug. 2003.
Office action in Chinese App. No. 201180050698.2 dated Dec. 3, 2014, 12 pages [English translation].
Office action in Chinese App. No. 201180050698.2 dated Mar. 13, 2014, 9 pages [English translation].
Office action in Chinese Application No. 201180050698.2, dated Aug. 7, 2015, 8 pages (with English translation).
Office action in European App. No. 11822676 dated Jul. 7, 2014, 3 pages.
Office action in European App. No. 11822676 dated Mar. 17, 2014, 4 pages.
Office action in Indian Application No. 2428/CHENP/2013, dated Jun. 25, 2018, 6 pages (Including English Translation).
Office action in Japanese App. No. 2013-527321, mailed Sep. 7, 2015, 6 pages [English translation].
Office action in U.S. Appl. No. 13/820,453 dated Jun. 19, 2014, 9 pages.
Office action in U.S. Appl. No. 13/820,453 dated Nov. 22, 2013, 7 pages.
Office action in U.S. Appl. No. 13/820,453 dated Sep. 24, 2015, 10 pages.
Office action in U.S. Appl. No. 14/209,369, dated Jun. 20, 2016, 12 pages.
Ohara et al., "Molecular Cloning and Sequence Determination of DA Strain of Theiler's Murin Encephalomyelitis Viruses," Virology, 1988, 164:245-255.
Okamoto et al., "Full-Length Sequence of a Hepatitis C Virus Genome Having Poor Homology to Reported Isolates; Comparative Study of Four Distinct Genotypes," Virology, 1992, 188:331-341.
Okuno et al., "Studies on the Use of Mumps Virus for Treatment of Human Cancer," Biken J., 1978, 21:37-49.
Ott et al., "Measurement of radiation dose to the thyroid using positron emission tomography," British Journal of Radiology, Mar. 1987, 60:245-251.
Paillard, "Bystander Effects in Enzyme/Prodrug Gene Therapy," Human Gene Ther., 1997, 8:1733-1736.
Palmenberg et al., "The nucleotide and deducted amino acid sequences of the encephalomyocarditis viral polyprotein coding region," Nucl. Acids Res., 1984, 12(6):2969-2985.
Parker et al., "Cancer Statistics, 1997," CA Cancer J. Clin., 1997, 47:5-27.
Paroder-Belenitsky et al., "Mechanism of anion selectivity and stoichiometry of the Na+/Isymporter (NIS)," Proc Natl Acad Sci U S A, vol. 108(44), Nov. 2011, pp. 17933-17938.
Pasquinucci, "Possible Effect of Measles on Leukemia," Lancet, 1971, 7690:136.
Paul et al., "The entire nucleotide sequence of the genome of human hepatitis A virus (isolate MBB)," Virus Res., 1987, 8:153-171.
Pedemonte et al., "Small-molecule correctors of defective DeltaF508-CFTR cellular processing identified by high-throughput screening," The Journal of Clinical Investigation, vol. 115(9), Sep. 2005, pp. 2564-2571.
Penheiter et al., "The Sodium Iodide Symporter (NIS) as an Imaging Reporter for Gene, Viral, and Cell-based Therapies," Current Gene Therapy., 12:33-47, 2012.
Penheiter et al., "Sodium Iodide Symporter (NIS)-Mediated Radiovirotherapy for Pancreatic Cancer," AJR American Journal of Roentgenology, vol. 195(2), Aug. 2010, pp. 341-349.
Pentlow et al., "Quantitative imaging of I-124 using positron emission tomography with applications to radioimmunodiagnosis and radioimmunotherapy," Med. Phys., 1991, 18(3):357-366.
Pentlow et al., "Quantitative Imaging of Iodine-124 with PET," J. Nucl. Med., 1996, 37:1557-1562.
Pevear et al., "Analysis of the Complete Nucleotide Sequence of the Picornavirus Theiler's Murine Encephalomyelitis Virus Indicates That It Is Closely Related to Cardioviruses," J. Virol., 1987, 61(5):1507-1516.
Philippou et al., "An ELISA for factor X activation peptide: application to the investigation of thrombogenesis in cardiopulmonary bypass," Br. J. Haematol., 1995, 90:432-437.
Polonsky et al., "Use of Biosynthetic Human C-peptide in the Measurement of Insulin Secretion Rates in Normal Volunteers and Type I Diabetic Patients," J. Clin. Invest., 1986, 77:98-105.
Racaniello and Baltimore, "Molecular cloning of poliovirus cDNA and determination of the complete nucleotide sequence of the viral genome," Proc. Natl. Acad. Sci. USA, 1981, 78(8):4887-4891.
Radecke et al., "Rescue of measles viruses from cloned DNA," EMBO J., 1995, 14(23):5773-5784.
Rathore and Batra, "Construction, expression and characterization of chimaeric toxins containing the ribonucleolytic toxin restrictocin: intracellular mechanism of action," Biochem J., 324 ( Pt 3):815-822, Jun. 15, 1997.
Reichard et al., "Newcastle Disease Virus Selectively Kills Human Tumor Cells," J. Surg. Res., 1992, 52:448-453.
Restriction requirement in U.S. Appl. No. 14/209,369 dated Dec. 2, 2015, 7 pages.
Rhoden et al., "Fluorescence quantitation of thyrocyte iodide accumulation with the yellow fluorescent protein variant YFP-H148Q/I152L," Anal Biochem., 373(2):239-46. Epub Oct. 22, 2007.
Rhoden et al., "Cell-based imaging of sodium iodide symporter activity with the yellow fluorescent protein variant YFP-H148Q/I152L," American Journal of Physiology Cell Physiology, vol. 292, Sep. 2006, pp. C814-823.
Richmond and Su., "Mouse Xenograft Models Vs GEM Models for Human Cancer Therapeutics," Disease Models & Mechanisms., 1(2-3):78-82, September-Oct. 2008.
Ritt et al., "Absolute quantification in SPECT," European Journal of Nuclear Medicine Imaging, vol. 38(1), 2011, pp. 69-77.
Robbins and Rapp, "Inhibition of Measles Virus Replication by Cyclic AMP," Virology, 1980, 106:317-326.
Robbins, "Stimulation of Measles Virus Replication by Cyclic Guanosine Monophosphate," Intervirology, 1991, 32:204-208.
Rokkones et al., "Expression of human parathyroid hormone in mammalian cells, *Escherichia coli* and *Saccharomyces cerevisiae*," J Biotechnol., 33(3):293-306, Apr. 15, 1994.
Rosenthal et al., "Paracrine Stimulation of Keratinocytes in Vivo and Continuous Delivery of Epidermal Growth Factor to Wounds in Vivo by Genetically Modified Fibroblasts transfected with a Novel Chimeric Construct," In Vivo, 1997, 11:201-208.
Rubello et al., "Parathyroid Imaging With Pertechnetate Plus Perchlorate/MIBI Subtraction Scintigraphy: A Fast and Effective Technique," Clinical Nuclear Medicine, vol. 25, 2000, pp. 527-531.
Rubin et al., "High-Resolution Positron Emission Tomography of Human Ovarian Cancer in Nude Rats Using 124I-Labeled Monoclonal Antibodies," Gyn. Oncol., 1993, 48:61-67.
Russell et al., "Use of Fusogenic Membrane Glycoproteins as Novel Therapeutic Transgenes in Gliomas," Proc. Am. Assoc. Cancer Res., 2000, 41:259, Abstract #1648.
Russell, "Building better (NIS expressing) oncolytic viruses," International Society of Cell and Gene therapy of Cancer (ISCGT), Cork, Ireland Sep. 2-4, 2009, 48 pages [slideshow].
Ryan et al., "The complete nucleotide sequence of enterovirus type 70: relationships with other members of the Picornaviridae,"Journal of General Virology, Oct. 1990, vol. 71(10), pp. 2291-2299.
Saloura et al., "Evaluation of an attenuated vesicular stomatitis virus vector expressing interferon-beta for use in malignant pleural mesothelioma: heterogeneity in interferon responsiveness defines potential efficacy," Hum Gene Ther., 21(1):51-64, Jan. 2010.
Sato et al., "Attenuated mumps virus therapy of carcinoma of the maxillary sinus," Int. J. Oral Surg., 1979, 8:205-211.
Schattner et al., "Persistent Viral Infection Affects Tumorigenicity of a Neuroblastoma Cell Line," Cell. Immunol., 1985, 90:103-114.
Schattner, "Therapeutic Role of Measles Vaccine in Hodgkin's Disease," Lancet, 1984, 8367:171.
Schirrmacher et al., "Human tumor cell modification by virus infection: an efficient and safe way to produce cancer vaccine with

(56) References Cited

OTHER PUBLICATIONS pleiotropic immune stimulatory properties when using Newcastle disease virus," Gene Therapy, 1999, 6:63-73.
Schirrmacher et al., "Immunization With Virus-Modified Tumor Cells," Sem. Oncol., 1998, 25(6):677-696.
Schnell et al., "The Minimal Conserved Transcription Stop-Start Signal Promotes Stable Expression of a Foreign Gene in Vesicular Stomatitis Virus," Journal of Virology, vol. 70(4), Apr. 1996, pp. 2318-2323.
Schubert et al., "Primary Structure of the Vesicular Stomatitis Virus Polymerase (L) Gene: Evidence for a High Frequency of Mutations"; J Virology., 51(2):505-514, Aug. 1984.
Schumacher et al., "Comparative analysis of IRES efficiency of dicistronic expression vectorsw in primary cells and permanent cell lines," 1999, Anim. Cell Tech., pp. 67-69.
Segni and Curro, "Tolerability of the trivalent vaccine "Triviraten Berna" in atopical children and those with a history of febrile convulsions," Giornale di Malattie Infettive e Parassitaric, 1992, 44(11):839-846 (Summary is in English).
Shoham et al., "Augmentation of Tumor Cell Immunogenicity by Viruses—An Approach to Specific Immunotherapy of Cancer," Nat. Immun. Cell Growth Regul., 1990, 9:165-172.
Simonson et al., "Synthesis and Processing of Genetically Modified Human Proinsulin by Rat Myoblast Primary Cultures," Human Gene Therapy, vol. 7, Jan. 1996, pp. 71-78.
Sinkovics and Horvath, "Can Virus Therapy of Human Cancer Be Improved by Apoptosis Induction," Medical Hypotheses, 1995, 44:359-368.
Sinkovics and Horvath, "Newcastle disease virus (NDV): brief history of its oncolytic strains," J. Clin. Virol., 2000, 16:1-15.
Sinkovics, "Oncogenes—Antioncogenes and Virus Therapy of Cancer," Anticancer Res., 1989, 9:1281-1290.
Sinkovics, "Viral Oncolysates as Human Tumor Vaccines," Intern. Rev. Immunol., 1991, 7:259-287.
Skern et al., "Human rhinovirus 2: complete nucleotide sequence and proteolytic processing signals in the capsid protein region," Nucl. Acids Res., 1985, 13(6):2111-2126.
Smanik et al., "Cloning of the Human Sodium Iodide Symporter," Biochem. Biophys. Res. Comm., 1996, 226:339-345.
Smanik et al., "Expression, Exon-Intron Organization, and Chromosome Mapping of the Human Sodium Iodide Symporter," Endocrinology, 1997, 138(8):3555-3558.
Smith et al., "Studies on the Use of Viruses in the Treatment of Carcinoma of the Cervix," Cancer, 1956, 9(6):1211-1218.
Smyth and Trapani, "Granzymes: exogenous proteinases that induce target cell apoptosis," Immunol. Today, 16(4):202-206, Apr. 1995.
Sonenberg and Meerovitch, "Translation of poliovirus mRNA," Enzyme, 1990, 44:278-291.
Spitzweg et al., "Analysis of Human Sodium Iodide Symporter Immunoreactivity in Human Exocrine Glands," J. Clin. Endocrinol. Metab., 1999, 84:4178-4184.
Spitzweg et al., "Prostrate-specific antigen (PSA) promoter-driven androgen-inducible expression of sodium iodide symporter in prostrate cancer cell lines," Cancer Res., 1999, 59:2136-2141.
Spitzweg et al., "Treatment of Prostate Cancer by Radioiodine Therapy after Tissue-specific Expression of the Sodium Iodide Symporter," Cancer Research, 2000, vol. 60, pp. 6526-6530.
Sporn et al., "Chemoprevention of Cancer," Carcinogenesis., 21(3):525-530, 2000.
Stanway et al., "Comparison of the complete nucleotide sequences of the genomes of the neurovirulent poliovirus P3/Leon/37 and its attenuated Sabin vaccine derivative P3/Leon/12alb," Proc. Natl. Acad. Sci. USA, 1984, 81:1539-1543.
Stojdl et al., "Exploiting tumor-specific defects in the interferon pathway with a previously unknown oncolytic virus," Nat Med., 6(7):821-825, Jul. 2000.
Stratagene Catalog. Gene Characterization kits. Stratage Catalog, pp. 39, 1988.
Strauss et al., "Fusion of Positron Emission Tomography (PET) and Gene Array Data: A New Approach for the Correlative Analysis of Molecular Biological and Clinical Data," IEEE Transactions on Medical Imaging, vol. 26(6), Jun. 2007, pp. 804-812.
Talanian et al., "Substrate Specificities of Caspase Family Proteases," J. Biol. Chem., 1997, 272(15):9677-9682.
Tanaka et al., "The hemagglutinin of recent measles virus isolates induces cell fusion in a marmoset cell line, but not in other CD46-positive human and monkey cell lines, when expressed together with the F protein," Arch Virol., 143(2):213-225, 1998.
Taqi et al., "Regression of Hodgkin's Disease After Measles," Lancet, 1981, 8223:1112.
Thoppil et al., "Terpenoids as Potential Chemopreventive And Therapeutic Agents In Liver Cancer," World J Hepatol., 3(9):228-249, Sep. 27, 2011.
Thornberry et al., "A Combinational Approach Defines Specificities of Members of the Caspase Family and Granzyme B," J. Biol. Chem., 1997, 272(29):17907-17911.
Tjuvajev et al., "Imaging Herpes Virus Thymidine Kinase Gene Transfer and Expression by Positron Emission Tomography," Cancer Res., 1998, 58:4333-4341.
Torigoe et al., "Application of Live Attenuated Measles and Mumps Vaccines in Children with Acute Leukemia," Biken J., 1981, 24:147-151.
Turner et al., "Broadened Clinical Utility of Gene Gun-Mediated, Granulocyte-Macrophage Colony-Stimulating Factor cDNA-Based Tumor Cell Vaccines as Demonstrated with a Mouse Myeloma Model," Human Gene Therapy, vol. 9(8), Mar. 2008, pp. 1121-1130.
Usonis et al., "Reactogenicity and immunogenicity of a new live attenuated combined measles, mumps and rubella vaccine in healthy children," Pediatr. Infect. Dis. J., 1999, 18:42-48.
Veelken et al., "Enhancement of a constitutively active promoter for gene therapy by a positive feedback transcriptional activator mechanism," Int J Mol Med., 2(4):423-428, Oct. 1998.
Veelken et al., "Systematic evaluation of chimeric marker genes on dicistronic transcription units for regulated expression of transgenes in vitro and in vivo," Hum. Gene Ther., 1996, 7:1827-1836.
Verma and Somia, "Gene therapy—promises, problems and prospects," Nature, 1997, 389:239-242.
Vial and Descotes, "Immune-mediated side-effects of cytokines in humans," Toxicology, 105(1):31-57, Dec. 20, 1995.
Von Hoegen et al., "Modification of tumor cells by a low dose of Newcastle Disease Virus," European Journal of Virology, 1988, 18(8), pp. 1159-1166.
Wall et al., "Transgenic Dairy Cattle: Genetic Engineering on a Large Scale," J. Dairy Sci., 1997, 80:2213-2224.
Walsh et al., "Investigating the use of the chymosin-sensitive sequence of κ-casein as a cleaveable linker site in fusion proteins," Journal of Biotechnology, vol. 45, 1996, pp. 235-241.
Weibel et al., "Combined live measles-mumps virus vaccine," Archives of Disease in Childhood, 1973, 48:532-536.
Weidmann et al., "Proteolytic cleavage of the fusion protin but not membrane fusion is required for measles virus-induced immunosuppression in vitro," J. Virol., 2000, 74(4):1985-1993.
Werb, "ECM and Cell Surface Proteolysis: Regulating Cellular Ecology," Cell, 1997, 91:439-442.
Wertz et al., "Adding genes to the RNA genome of vesicular stomatitis virus: positional effects on stability of expression," J Virol., 76(15):7642-7650, Aug. 2002.
Whelan et al., "Efficient recovery of infectious vesicular stomatitis virus entirely from cDNA clones," Proc Natl Acad Sci U S A., 92(18):8388-8392, Aug. 29, 1995.
Whelen et al., "Transcription and Replication of Nonsegmented Negative-Strand RNA Viruses," Biology of Negative Strand RNA Viruses: The Power of Reverse Genetics, Springer-Verlag Berlin Heidelberg, vol. 283, pp. 61-119, 2004.
Wilson C et al., "Formation of Infectious Hybrid Virion with Gibbon Ape Leukemia Virus and Human T-Cell Leukemia Virus Retroviral Envelope Glycoproteins and the gag and pol Proteins of Moloney Murine Leukemia Virus," Journal of Virology, vol. 63(5) May 1989, pp. 2374-2378.
Wilson et al., "Random Mutagenesis by PCR," Current Protocols in Molecular Biology, Chapter 8, Unit 8, May 2001.
Wolfsberg et al., "ADAM, a Novel Family of Membrane Proteins Containing A Disintegrin And Metalloprotease Domain: Multipotential

(56) References Cited

OTHER PUBLICATIONS

Functions in Cell-Cell and Cell-Matrix Interactions," J Cell Biol., Oct. 1995, vol. 131(2), pp. 275-278.
World Health Organization Technical Report Series, "WHO Expert Committee on Biological Standardization," Forty-third Report, 1994, No. 840, pp. 102-120.
Wunderlich et al., "Preincubation with Sn-complexes causes intensive intracellular retention of 99mTc in thyroid cells in vitro," Nuklearmedizin, vol. 51(5), 2012, pp. 179-185.
Wyde et al., "Infection of leucocytes by measles vaccine viruses Edmonston-Zagreb and Enders-Moraten has different consequences: potential mechanism for increased vaccine efficacy or aberrant activity in field trials," Vaccine, Jun. 1994, vol. 12(8), pp. 715-722.
Yamamoto et al., "Isolation of a cDNA Encoding a Human Serum Marker for Acute Pancreatitis," J. Biol. Chem., 1992, 267(4):2575-2581.
Yamashita et al., "Crystal structure of a bacterial homologue of Na+/Cl−-dependent neurotransmitter transporters," Nature, 437(7056):215-223, Epub Jul. 24, 2005.
Yao et al., "Proteolytic Processing of Rubella Virus Nonstructural Proteins," Virology, vol. 246, 1998, pp. 74-82.
Zwitter, "Hodgkin's Disease: Therapeutic Role of Measles Vaccine," The American Journal of Medicine, Dec. 1984, vol. 77(6), pp. A49-A54.
Zygiert, "Hodgkin's Dease: Remissions after Measles," Lancet, 1971, 7699:593.

* cited by examiner

FIG. 3A
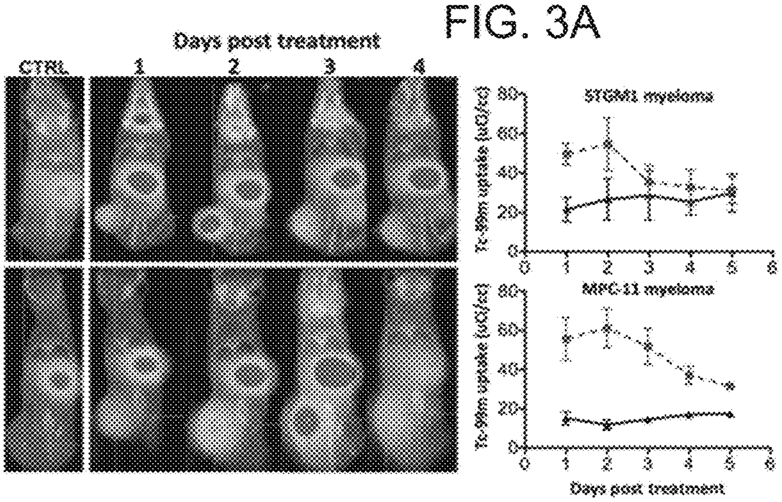
FIG. 3B
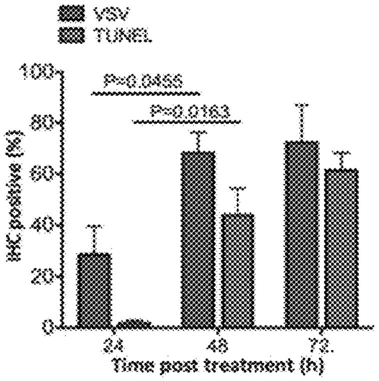
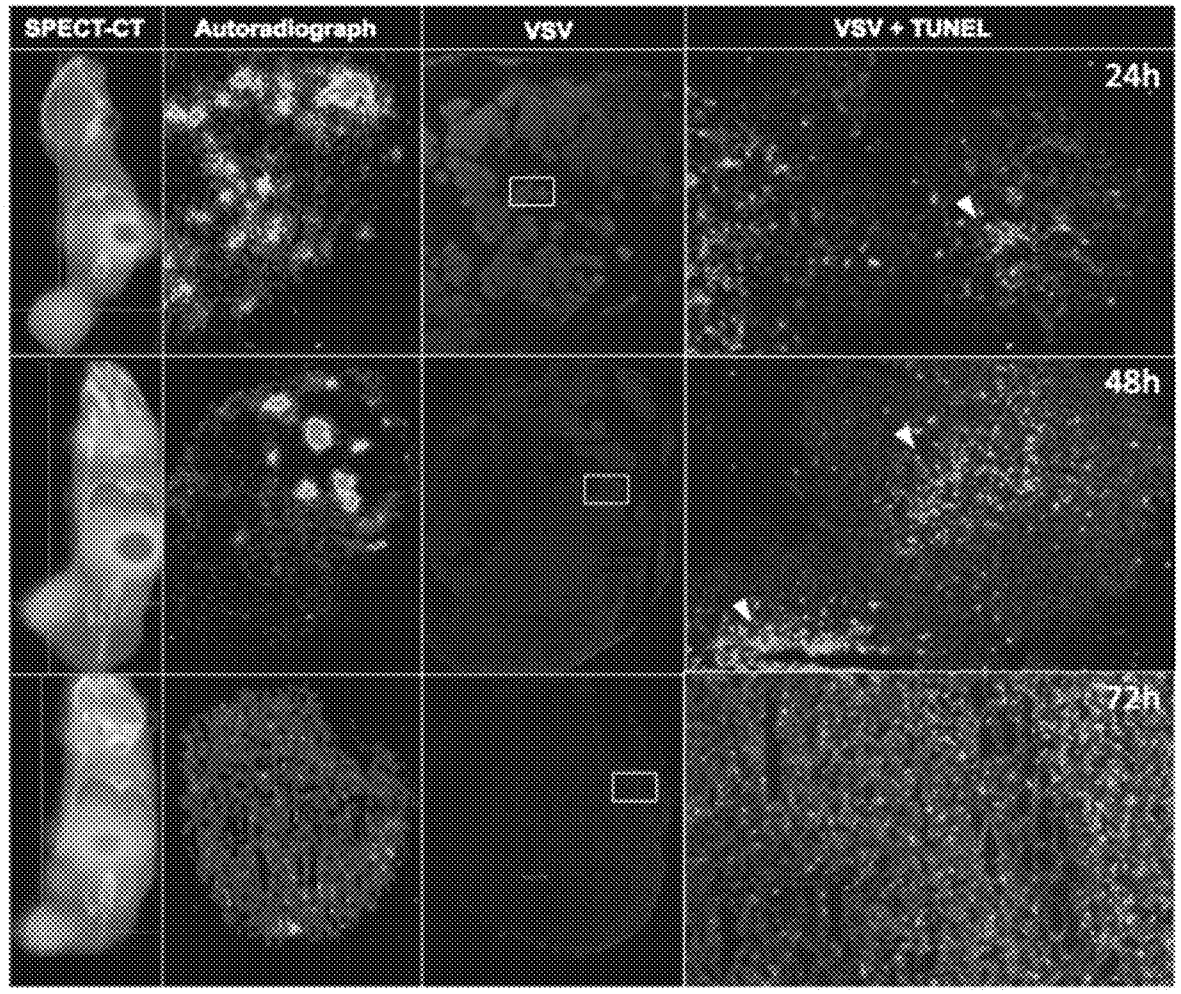
FIG. 3C

Life SPECT-CT Imaging 24h post VSV-IFN-NIS IV Treatment shows robust NIS expression. Corollary analysis of Harvested tumor Shows extensive intra-tumoral VSV infection And functional NIS expression

VESICULAR STOMATITIS VIRUSES

CROSS-REFERENCE TO RELATED APPLICATION

This application is a continuation of U.S. application Ser. No. 16/916,482, filed Jun. 30, 2020 (now U.S. Pat. No. 11,634,469), which is a continuation of U.S. application Ser. No. 15/925,279, filed Mar. 19, 2018 (now U.S. Pat. No. 10,752,666), which is a continuation of U.S. application Ser. No. 15/246,189, filed Aug. 24, 2016 (now U.S. Pat. No. 9,951,117), which is a divisional of U.S. application Ser. No. 13/820,453 (now U.S. Pat. No. 9,428,736), filed May 20, 2013, which is a National Stage Application under 35 U.S.C. § 371 of International Application No. PCT/US2011/050227, filed Sep. 1, 2011, which claims the benefit of U.S. Provisional Application No. 61/379,644, filed Sep. 2, 2010. The contents of the foregoing application are hereby incorporated by reference in their entirety.

STATEMENT AS TO FEDERALLY SPONSORED RESEARCH

This invention was made with government support under grant number CA129966 awarded by the National Institute of Health. The government has certain rights in the invention.

SEQUENCE LISTING

This application contains a Sequence Listing that has been submitted electronically as an XML file named "40083-0002005_SL_ST26.XML." The XML file, created on Mar. 13, 2023, is 2,288 bytes in size. The material in the XML file is hereby incorporated by reference in its entirety.

BACKGROUND

1. Technical Field

This document relates to methods and materials involved in making and using vesicular stomatitis viruses. For example, this document relates to vesicular stomatitis viruses, nucleic acid molecules, methods for making vesicular stomatitis viruses, and methods for using vesicular stomatitis viruses to treat cancer.

2. Background Information

Vesicular stomatitis virus (VSV) is a member of the Rhabdoviridae family. The VSV genome is a single molecule of negative-sense RNA that encodes five major polypeptides: a nucleocapsid (N) polypeptide, a phosphoprotein (P) polypeptide, a matrix (M) polypeptide, a glycoprotein (G) polypeptide, and a viral polymerase (L) polypeptide.

SUMMARY

This document provides methods and materials related to vesicular stomatitis viruses. For example, this document provides vesicular stomatitis viruses, nucleic acid molecules encoding VSV polypeptides, methods for making vesicular stomatitis viruses, and methods for using vesicular stomatitis viruses to treat cancer.

As described herein, vesicular stomatitis viruses can be designed to have a nucleic acid molecule that encodes a VSV N polypeptide, a VSV P polypeptide, a VSV M polypeptide, a VSV G polypeptide, a VSV L polypeptide, an interferon (IFN) polypeptide (e.g., a human IFN-0 polypeptide), and a sodium iodide symporter (NIS) polypeptide (e.g., a human NIS polypeptide). The nucleic acid encoding the IFN polypeptide can be positioned between the nucleic acid encoding the VSV M polypeptide and the nucleic acid encoding the VSV G polypeptide. Such a position can allow the viruses to express an amount of the IFN polypeptide that is effective to activate anti-viral innate immune responses in non-cancerous tissues, and thus alleviate potential viral toxicity, without impeding efficient viral replication in cancer cells. The nucleic acid encoding the NIS polypeptide can be positioned between the nucleic acid encoding the VSV G polypeptide and the VSV L polypeptide. Such a position of can allow the viruses to express an amount of the NIS polypeptide that (a) is effective to allow selective accumulation of iodide in infected cells, thereby allowing both imaging of viral distribution using radioisotopes and radiotherapy targeted to infected cancer cells, and (b) is not so high as to be toxic to infected cells. Positioning the nucleic acid encoding an IFN polypeptide between the nucleic acid encoding the VSV M polypeptide and the nucleic acid encoding the VSV G polypeptide and positioning the nucleic acid encoding a NIS polypeptide between the nucleic acid encoding the VSV G polypeptide and the VSV L polypeptide within the genome of a vesicular stomatitis virus can result in vesicular stomatitis viruses that are viable, that have the ability to replicate and spread, that express appropriate levels of functional IFN polypeptides, and that expression appropriate levels of functional NIS polypeptides to take up radio-iodine for both imaging and radio-virotherapy.

In some cases, this document features a vesicular stomatitis virus comprising an RNA molecule. The RNA molecule comprises, or consists essentially of, in a 3' to 5' direction, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding an IFN polypeptide, a nucleic acid sequence that is a template for a positive sense transcript encoding a VSV G polypeptide, a nucleic acid sequence that is a template for a positive sense transcript encoding a NIS polypeptide, and a nucleic acid sequence that is a template for a positive sense transcript encoding a VSV L polypeptide. The IFN polypeptide can be a human IFN beta polypeptide. The NIS polypeptide can be a human NIS polypeptide. The virus can express the IFN polypeptide when the virus infects a mammalian cell. The virus can express the NIS polypeptide when the virus infects a mammalian cell.

In another aspect, this document features a composition comprising, or consisting essentially of, a vesicular stomatitis virus comprising RNA molecule. The RNA molecule comprises, or consists essentially of, in a 3' to 5' direction, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding an IFN polypeptide, a nucleic acid sequence that is a template for a positive sense transcript encoding a VSV G polypeptide, a nucleic acid sequence that is a template for a positive sense transcript encoding a NIS polypeptide, and a nucleic acid sequence that is a template for a positive sense transcript encoding a VSV L polypeptide. The IFN polypeptide can be a human IFN beta polypeptide. The NIS polypeptide can be a human NIS polypeptide. The virus can express the IFN polypeptide when the virus infects a mammalian cell. The virus can express the NIS polypeptide when the virus infects a mammalian cell.

In another aspect, this document features a nucleic acid molecule comprising a nucleic acid strand comprising, or consisting essentially of, in a 3' to 5' direction, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding an IFN polypeptide, a nucleic acid sequence that is a template for a positive sense transcript encoding a VSV G polypeptide, a nucleic acid sequence that is a template for a positive sense transcript encoding a NIS polypeptide, and a nucleic acid sequence that is a template for a positive sense transcript encoding a VSV L polypeptide. The IFN polypeptide can be a human IFN beta polypeptide. The NIS polypeptide can be a human NIS polypeptide.

In another aspect, this document features a method for treating cancer. The method comprises, or consists essentially of, administering a composition comprising vesicular stomatitis viruses to a mammal comprising cancer cells. The vesicular stomatitis viruses comprise an RNA molecule comprising, or consisting essentially of, in a 3' to 5' direction, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding an IFN polypeptide, a nucleic acid sequence that is a template for a positive sense transcript encoding a VSV G polypeptide, a nucleic acid sequence that is a template for a positive sense transcript encoding a NIS polypeptide, and a nucleic acid sequence that is a template for a positive sense transcript encoding a VSV L polypeptide, wherein administration of the composition to the mammal is under conditions wherein the vesicular stomatitis viruses infect the cancer cells to form infected cancer cells, wherein the infected cancer cells express the IFN polypeptide and the NIS polypeptide, and wherein the number of cancer cells within the mammal is reduced following the administration. The mammal can be a human. The IFN polypeptide can be a human IFN beta polypeptide. The NIS polypeptide can be a human NIS polypeptide.

In another aspect, this document features a method for inducing tumor regression in a mammal. The method comprises, or consists essentially of, administering a composition comprising vesicular stomatitis viruses to a mammal comprising a tumor. The vesicular stomatitis viruses comprises an RNA molecule comprising, or consisting essentially of, in a 3' to 5' direction, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding an IFN polypeptide, a nucleic acid sequence that is a template for a positive sense transcript encoding a VSV G polypeptide, a nucleic acid sequence that is a template for a positive sense transcript encoding a NIS polypeptide, and a nucleic acid sequence that is a template for a positive sense transcript encoding a VSV L polypeptide, wherein administration of the composition to the mammal is under conditions wherein the vesicular stomatitis viruses infect tumor cells of the tumor to form infected tumor cells, wherein the infected tumor cells express the IFN polypeptide and the NIS polypeptide.

The mammal can be a human. The IFN polypeptide can be a human IFN beta polypeptide. The NIS polypeptide can be a human NIS polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic diagram of the genome arrangement of an exemplary vesicular stomatitis virus containing nucleic acid encoding an IFN polypeptide (e.g., a human or mouse IFNβ polypeptide) and nucleic acid encoding a NIS polypeptide (e.g., a human NIS polypeptide). FIG. 1B is a graph plotting the viral titer of vesicular stomatitis viruses containing nucleic acid encoding a green fluorescent protein (GFP) polypeptide (VSV-GFP; (•)), VSV-mIFN-NIS (■), or VSV-hIFN-NIS (♦) determined using BHK cells infected at MOI 1.0. FIG. 1C is a graph plotting radio-iodide uptake of cells infected with VSV-mIFN-NIS or VSV-hIFN-NIS in the presence or absence of KCLO4, a NIS inhibitor (+inh.). VSV-GFP was used as a control. FIG. 1D contains bar graphs plotting the level of secretion of murine or human IFNβ measured by ELISA from mock infected cells or cells infected with VSV-mIFN-NIS (VmN) or VSV-hIFN-NIS (VhN). FIG. 1E contains bar graphs plotting IFN responsiveness of 5TGM1 and MPC-11 murine myeloma cells compared to B-16 murine melanoma cells as assessed by pre-treating cells with 100 U/mL murine IFNβ for 12 hours, followed by infection with VSV-GFP (MOI 1.0). FIG. 1F contains graphs plotting proliferation of viable cells results assessed by an MT assay at 48 hours post-infection (plotted as % of untreated cells). 5TGM1 and MPC-11 oncolysis was monitored following infection with VSV-mIFN-NIS or VSV-hIFN-NIS (MOI 1.0) by measuring cell viability at 12 hour intervals by MTT assay.

FIG. 2A is a graph plotting the level of IFN polypeptide release from BHK cells infected with either VSV-mIFN-NIS or VSV-mIFN and monitored over a 48 hour time period. The mouse IFN polypeptide levels were measured in the supernatant using an ELISA designed to detect mouse IFN polypeptides expression levels. FIG. 2B is a graph plotting the level of I-125 uptake by BHK cells infected with either VSV-mIFN-NIS or VSV-mIFN at the indicated time (hours).

FIGS. 3A-3C contain results from monitoring intratumoral spread of intravenously administered VSV-IFN-NIS. Female, 6-10 week old C57B16/KaLwRij mice bearing subcutaneous syngeneic 5TGM1 myeloma tumors were treated with a single intravenous (IV) dose of 100 μL PBS (control) or $1\times10^8$ $TCID_{50}$ VSV-mIFN-NIS. (A) SPECT-CT imaging was carried out at 24 hour intervals post-treatment following administration with 0.5 mCi Tc-99m. Tumor specific Tc-99m uptake was quantified in PBS treated mice (n=2) and VSV-mIFN-NIS treated mice (n=5). (B) Intratumoral viral distribution was monitored by harvesting tumors following SPECT-CT imaging and corollary analysis of adjacent tumor section by autoradiography, and IF was performed.

IF was used to detect VSV antigens (which stained red) and cells undergoing cell death by TUNEL staining (which stained green) at 24 hour time periods. (C) Intratumoral VSV and TUNEL were quantified using from 4 images from n=3 tumors (n=2 at 72 hours) using ImageJ software and shown as a percentage of tumor area. There was a significant increase in both VSV(+) and TUNEL(+) between 24 and 48 hours post treatment using t-test (P=0.0455 and P=0.0163, respectively).

FIGS. 4A-4D contain results of intratumoral viral entry, spread, and oncolysis following intravenous delivery. (A) 5TGM1 tumors were harvested and analyzed by IF at (i) 6 hours, (ii) 12 hours, (iii) 18 hours, and (iv-vi) 24 hours following intravenous VSV-mIFN-NIS administration indicating VSV infected cells (which stained green) and tumor blood vessels by CD31 staining (which stained red). Magnification 100×. (B) High magnification view of treated tumors showing intact tumor blood vessels (which stained red) in proximity of (i) VSV infected tumor cells (which stained green) and (ii) TUNEL positive cells undergoing cells death (which stained green) with Hoescht stained nuclei (which stained blue). (C) Intratunoral foci (n=8) from tumors harvested at 6 hour intervals were measured using ImageJ software, and average diameter was plotted over time. Significance of diameter growth was measured by t-test, and P values are shown along the top of the graph. Diameters were used to measure average foci volume over time. (D) Images of tumor at 48 hours post VSV-mIFN-NIS treatment were used to quantify viable rim of infected cells to obtain an average of ~10 cells being infected at each round of infection prior to cell death.

Figure 5:
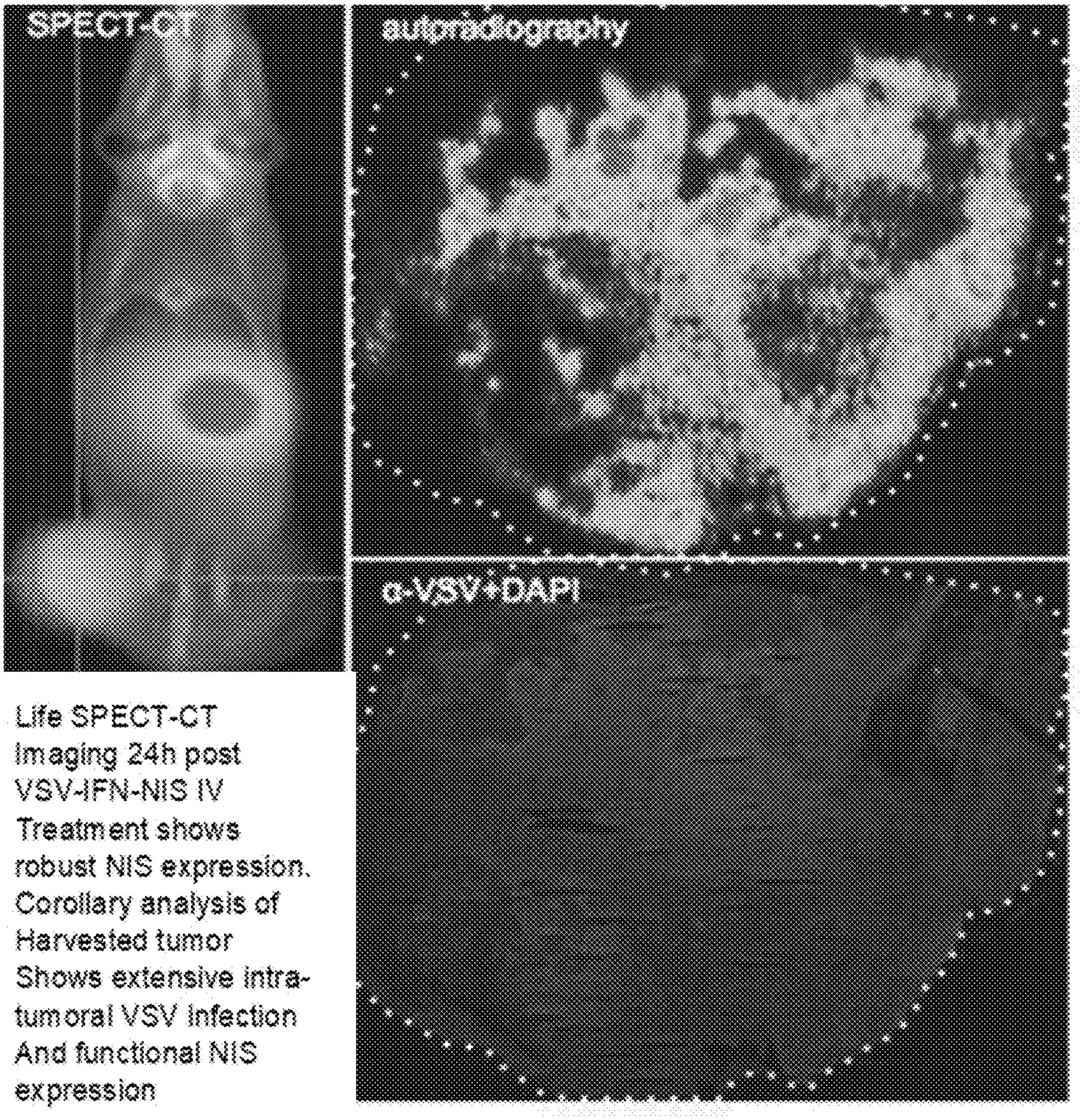

FIG. 5 contains a set of three images of a tumor from the same mouse, undergoing whole body SPECT-CT imaging to monitor viral distribution (top, left), tumor autoradiography to show specific regions of radio-isotope uptake (top, right), and anti-VSV and DAPI staining to show that regions of NIS expression correspond to intratumoral VSV staining (bottom).

Figure 6A:
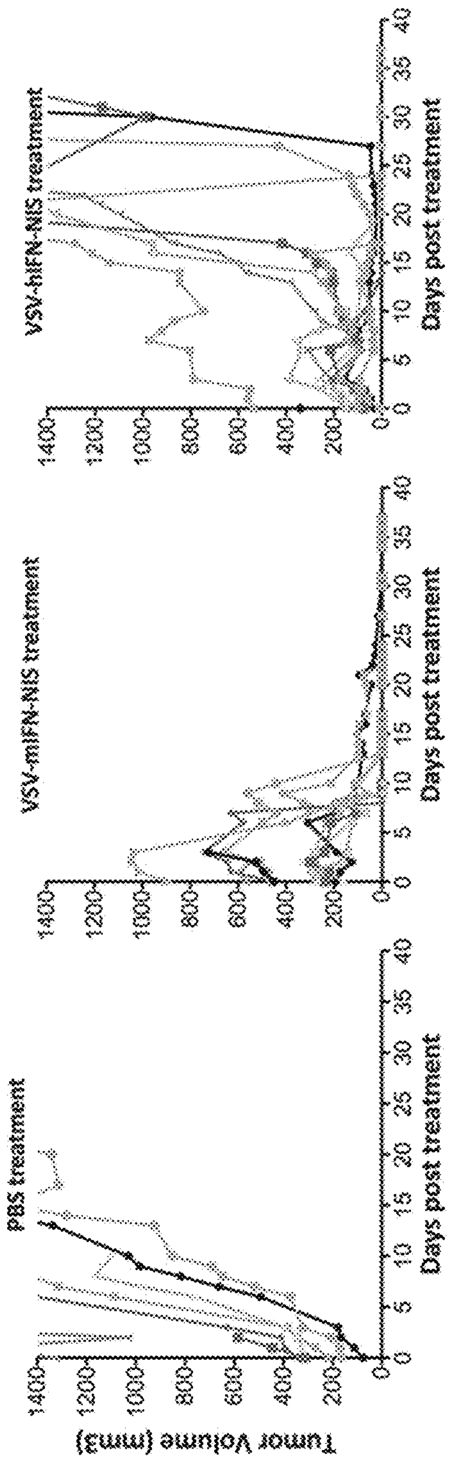
Figure 6B:
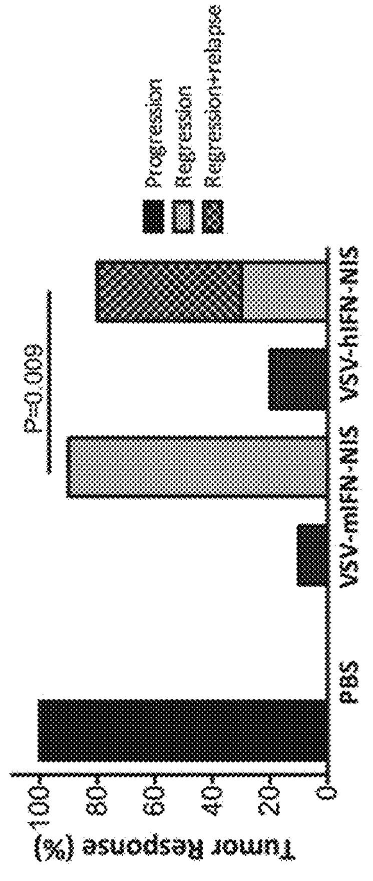
Figure 6C:
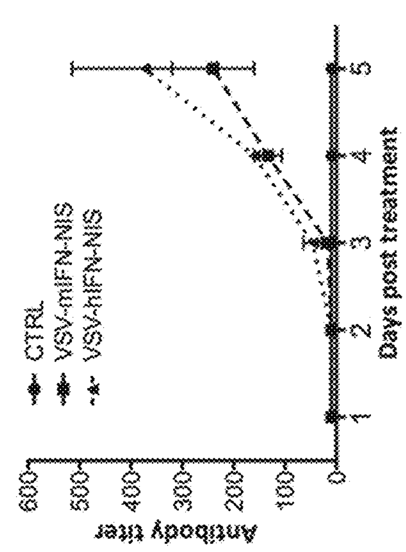

FIGS. 6A-6C contain results demonstrating a potent therapeutic efficacy of systemically administered VSV-IFN-NIS. Mice bearing subcutaneous 5TGM1 tumors were treated with a single intravenous dose of PBS, VSV-mIFN-NIS, or VSV-hIFN-NIS. (A) Tumor burden was measured by serial caliper measurements to calculate tumor volume over time. (B) Tumor responses were categorized into tumor progression, regression, or regression with relapse. Statistical difference in incidence of relapse as proportion of mice with tumor regression was measured Fischer Exact test indicating significantly higher rate of tumor relapse in VSV-hIFN-NIS treated mice vs. VSV-mIFN-NIS treated mice (P=0.009). (C) Generation of VSV neutralizing antibodies was measured in serum of n=2 (PBS treated) and n=3 (VSV-IFN-NIS treated) mice in the first 5 days post treatment and plotted as the minimum fold dilution that protects from infection with 500 $TCID_{50}$ VSV.

FIGS. 7A-7E contain results demonstrating that immune mediated elimination of tumor cells prevents tumor relapse. (A) Quantification of murine IFNβ in serum of mice bearing subcutaneous 5TGM1 tumors treated intravenously with PBS, VSV-mIFN-NIS, or VSV-hIFN-NIS measured by ELISA. (B) Mice that had complete tumor regression in response to VSV-mIFN-NIS treatment and naïve age-matched syngeneic mice (n=6 each) were challenged with $1\times10^7$ 5TGM1 cells subcutaneously, and tumor occurrence by day 21 post challenge is shown. (C) Immunotherapeutic efficacy of single dose VSV-infected 5TGM1 cells administered subcutaneously ($1\times10^7$ 5TGM1 cells infected with VSV-mIFN-NIS at MOI 10 implanted on left flank) at 1 day post or 5 days prior to tumor implantation ($5\times10^6$ subcutaneous 5TGM1 cells on right flank). Log rank survival analysis comparison revealed day (−5) vaccination prolongs survival of mice following tumor implantation compared to unvaccinated mice (P=0.0253). (D) Mice bearing subcutaneous 5TGM1 tumors were treated with single intravenous dose of (i) PBS, (ii) VSV-mIFN-NIS, or (iii) VSV-mIFN-NIS in the presence or absence of antibodies to deplete $CD4^+$ or $CD8^+$ T cells. Tumor burden was measured by serial caliper measurements. (E) Tumor responses for the mice described in FIG. 7D were categorized into progression, regression, or regression+relapse. Relapse rates were compared by Fischer Exact test indicating that VSV-mIFN-NIS+T-cell depletion exhibited a higher rate of tumor relapse compared to VSV-mIFN-NIS treatment alone (P=0.0498).

Figure 8B:
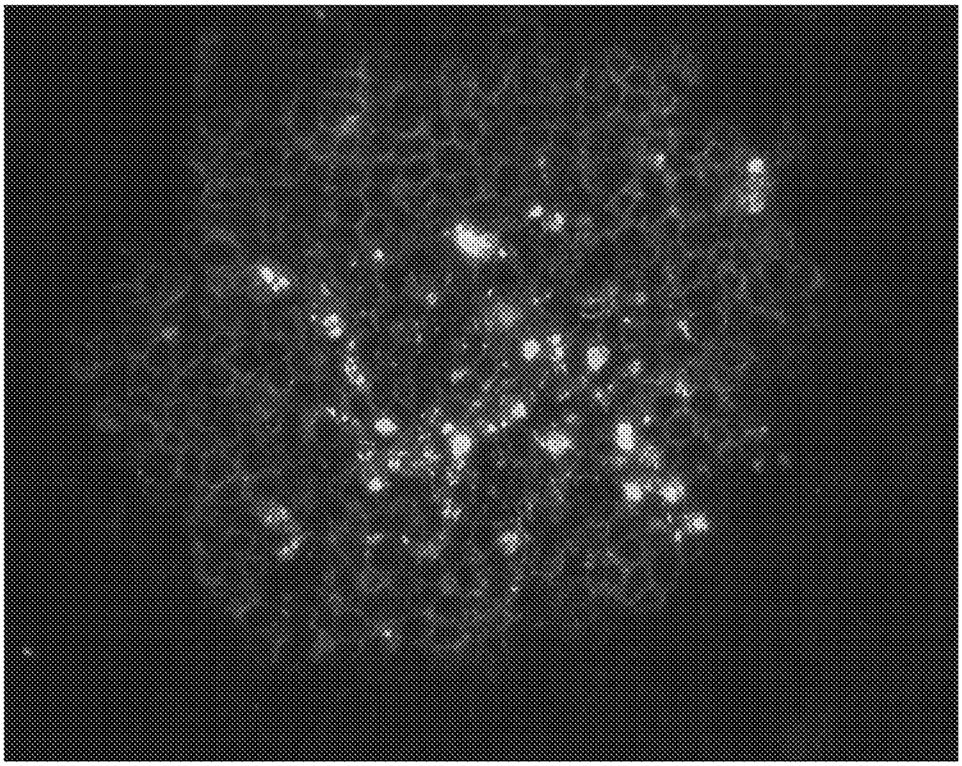
Figure 8A:
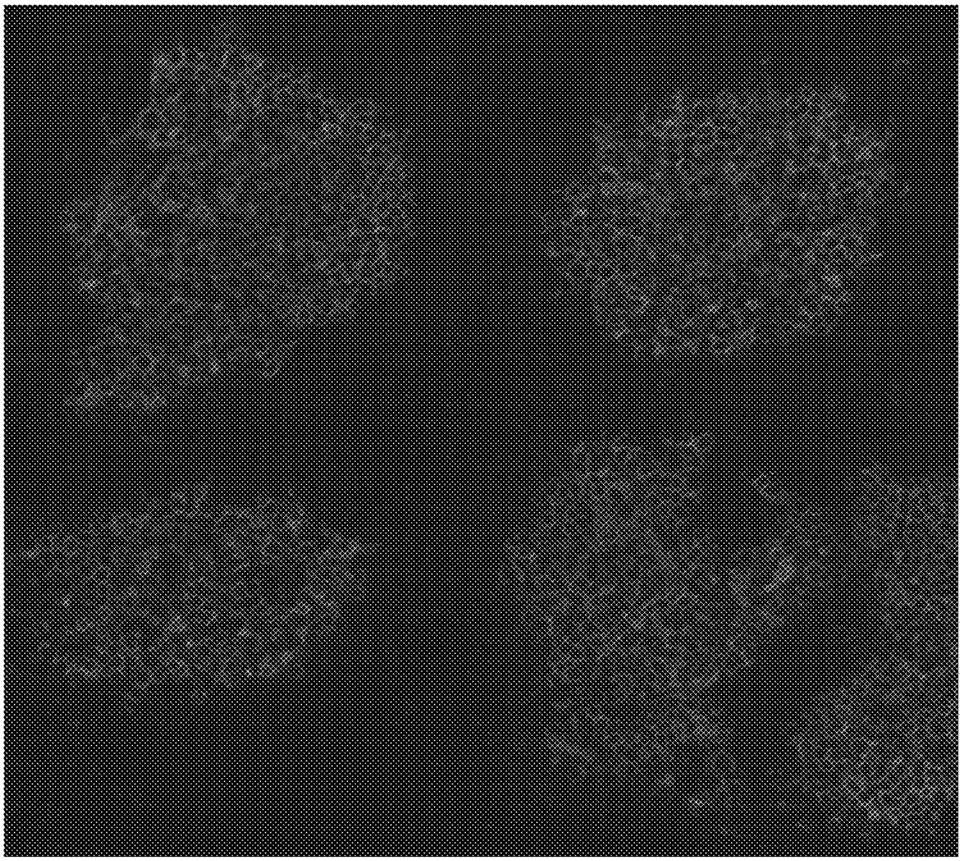

FIGS. 8A and 8B are detailed immunofluorescence images of intratumoral foci of infection. A 5TGM1 tumor was harvested 24 hours post intravenous VSV-mIFN-NIS injection, frozen in OCT, and sectioned. IF was performed to detect VSV (which stained red), dying cells by TUNEL staining (which stained green), and tumor cell nuclei by Hoescht staining (which stained blue). Distinct roughly spherical intratumoral foci of VSV infection contain a central region of VSV infected cells undergoing cell death and a rim of infected, viable cells in the periphery.

Figure 9A:
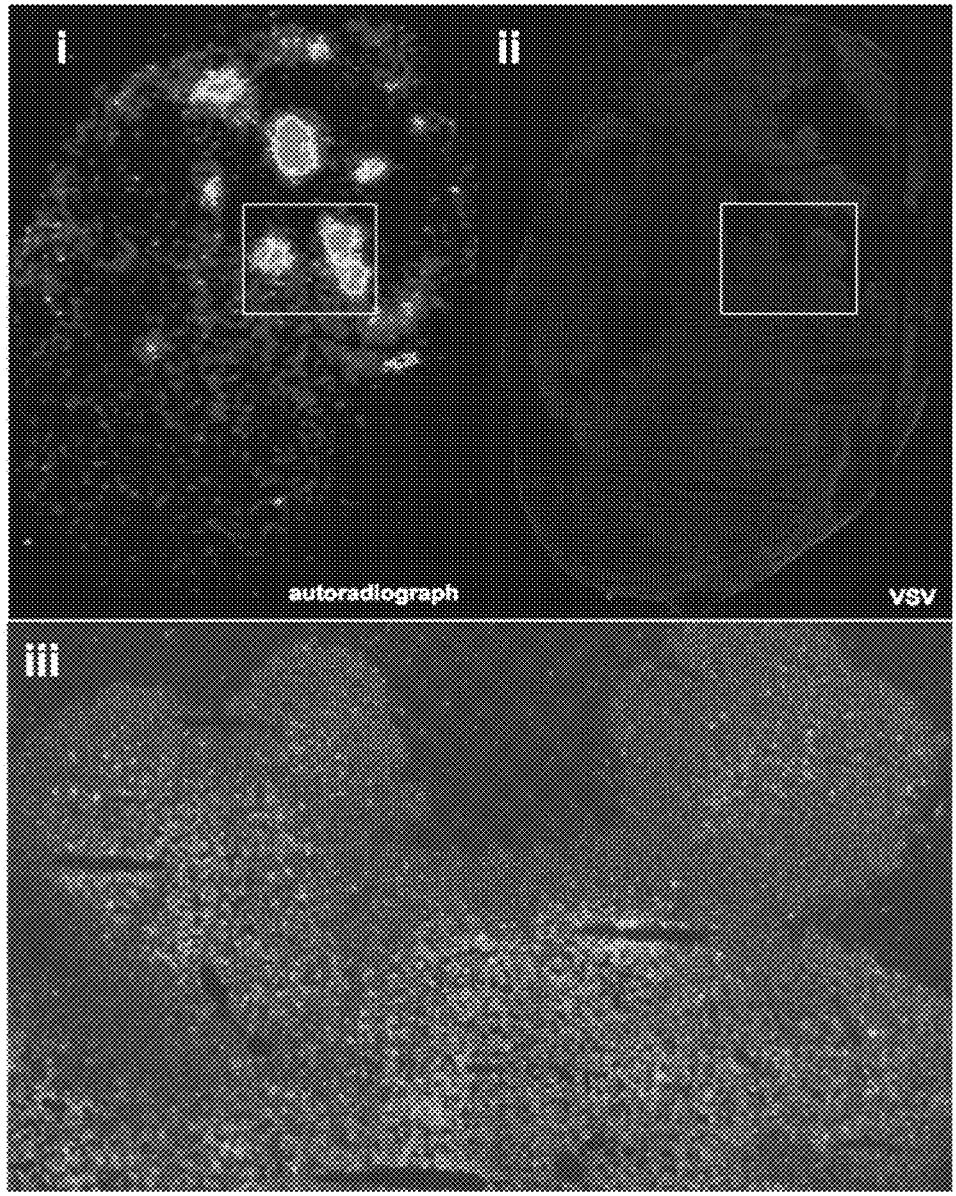
Figure 9B:
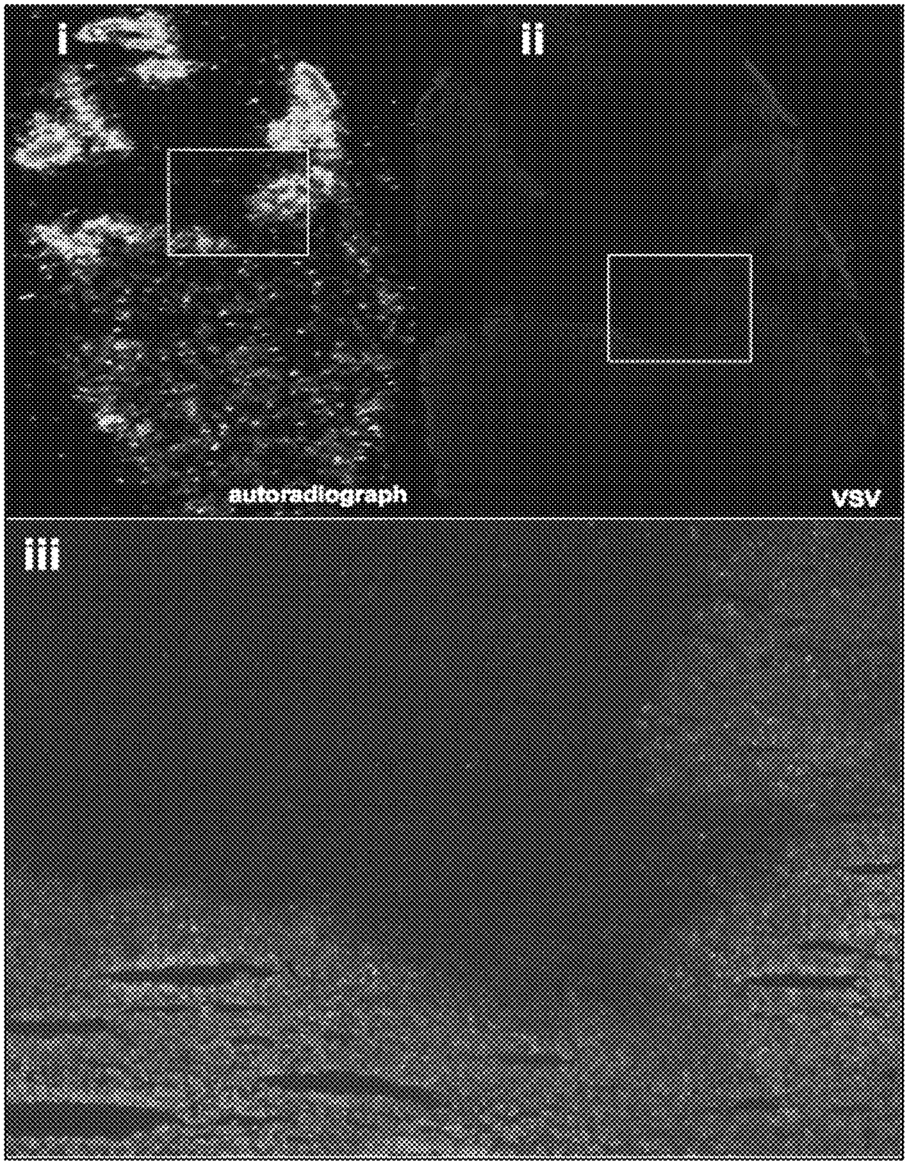

FIGS. 9A-9B contain images demonstrating that functional NIS activity is limited to regions of VSV infected viable cells. 5TGM1 tumors were harvested at 48 hours (A) or 72 hours (B) post intravenous VSV-IFN-NIS injection and sectioned. Adjacent sections were subject to (i) autoradiography, (ii) IF shown at 20× magnification, and (iii) IF shown at 100× magnification to detect VSV (which stained red) and dying cells by TUNEL staining (which stained green).

Figure 10:
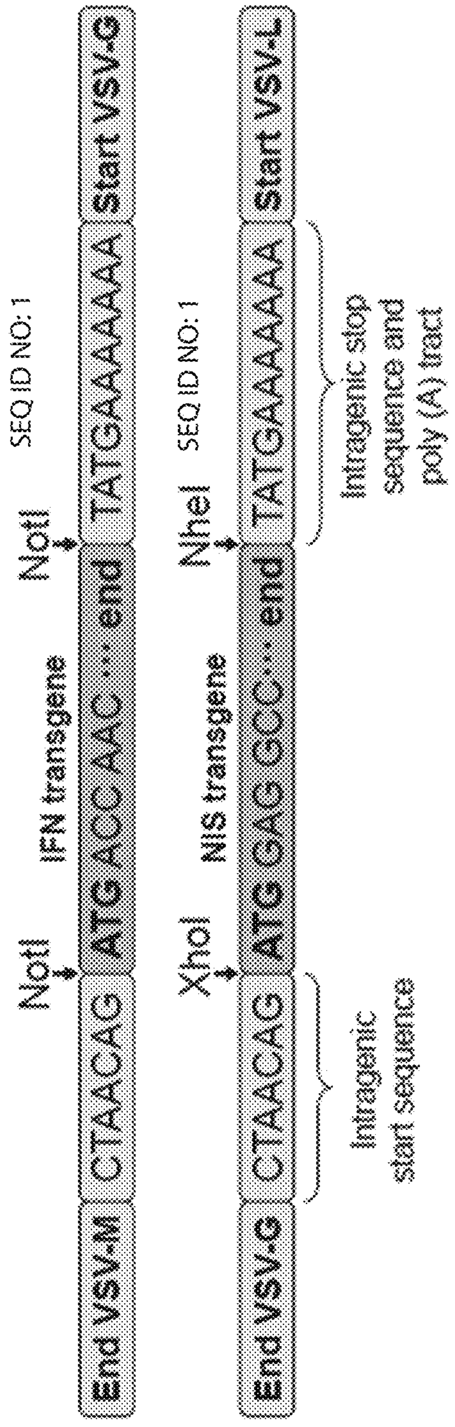

FIG. 10 is a diagram of exemplary intragenic regions of vesicular stomatitis viruses that contain inserted transgenes. The transgenes are flanked by viral start and stop sequences involved in transcription. The IFN nucleic acid is inserted into a NotI cloning site engineered between the VSV M and G nucleic acid sequences. The NIS nucleic acid is inserted into XhoI and NheI restriction sites engineered between the VSV G and L nucleic acid sequences.

DETAILED DESCRIPTION

This document provides methods and materials related to vesicular stomatitis viruses. For example, this document provides vesicular stomatitis viruses, nucleic acid molecules encoding VSV polypeptides, methods for making vesicular stomatitis viruses, and methods for using vesicular stomatitis viruses to treat cancer.

As described herein, a vesicular stomatitis virus can be designed to have a nucleic acid molecule that encodes a VSV N polypeptide, a VSV P polypeptide, a VSV M polypeptide, a VSV G polypeptide, a VSV L polypeptide, an IFN polypeptide, and a NIS polypeptide. It will be appreciated that the sequences described herein with respect to a vesicular stomatitis virus are incorporated into a plasmid coding for the positive sense cDNA of the viral genome allowing generation of the negative sense genome of vesicular stomatitis viruses. Thus, it will be appreciated that a nucleic acid sequence that encodes a VSV polypeptide, for example, can refer to an RNA sequence that is the template for the positive sense transcript that encodes (e.g., via direct translation) that polypeptide.

Figures 1A, 1B, 1C, 1D, 1E, 1F:
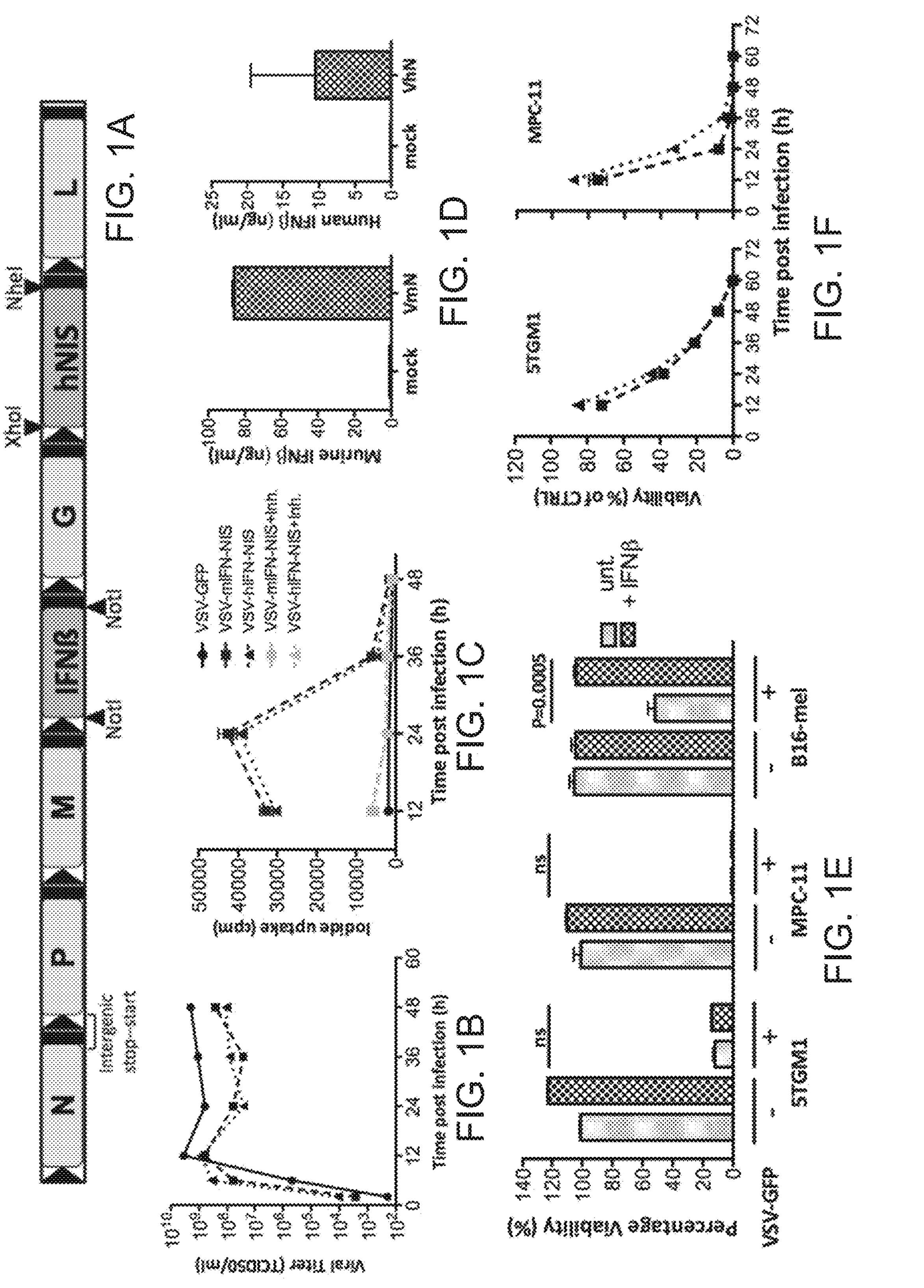
FIGS. 1A-1F.

The nucleic acid encoding the IFN polypeptide can be positioned downstream of the nucleic acid encoding the VSV M polypeptide (FIG. 1A). For example, nucleic acid encoding the IFN polypeptide can be positioned between the nucleic acid encoding the VSV M polypeptide and the nucleic acid encoding the VSV G polypeptide. Such a position can allow the viruses to express an amount of the IFN polypeptide that is effective to activate anti-viral innate immune responses in non-cancerous tissues, and thus alleviate potential viral toxicity, without impeding efficient viral replication in cancer cells.

Any appropriate nucleic acid encoding an IFN polypeptide can be inserted into the genome of a vesicular stomatitis virus. For example, nucleic acid encoding an IFN beta polypeptide can be inserted into the genome of a vesicular stomatitis virus. Examples of nucleic acid encoding IFN beta polypeptides that can be inserted into the genome of a vesicular stomatitis virus include, without limitation, nucleic acid encoding a human IFN beta polypeptide of the nucleic acid sequence set forth in GenBank® Accession No. NM_002176.2 (GI No. 50593016), nucleic acid encoding a mouse IFN beta polypeptide of the nucleic acid sequence set forth in GenBank® Accession Nos. NM_010510.1 (GI No. 6754303), BC119395.1 (GI No. 111601321), or BC119397.1 (GI No. 111601034), and nucleic acid encoding a rat IFN beta polypeptide of the nucleic acid sequence set forth in GenBank® Accession No. NM_019127.1 (GI No. 9506800).

The nucleic acid encoding the NIS polypeptide can be positioned downstream of the nucleic acid encoding the VSV G polypeptide (FIG. 1A). For example, nucleic acid encoding the NIS polypeptide can be positioned between the nucleic acid encoding the VSV G polypeptide and the nucleic acid encoding the VSV L polypeptide. Such a position of can allow the viruses to express an amount of the NIS polypeptide that (a) is effective to allow selective accumulation of iodide in infected cells, thereby allowing both imaging of viral distribution using radioisotopes and radiotherapy targeted to infected cancer cells, and (b) is not so high as to be toxic to infected cells.

Any appropriate nucleic acid encoding a NIS polypeptide can be inserted into the genome of a vesicular stomatitis virus. For example, nucleic acid encoding a human NIS polypeptide can be inserted into the genome of a vesicular stomatitis virus. Examples of nucleic acid encoding NIS polypeptides that can be inserted into the genome of a vesicular stomatitis virus include, without limitation, nucleic acid encoding a human NIS polypeptide of the nucleic acid sequence set forth in GenBank® Accession Nos. NM_000453.2 (GI No. 164663746), BC105049.1 (GI No. 85397913), or BC105047.1 (GI No. 85397519), nucleic acid encoding a mouse NIS polypeptide of the nucleic acid sequence set forth in GenBank® Accession Nos. NM_053248.2 (GI No. 162138896), AF380353.1 (GI No. 14290144), or AF235001.1 (GI No. 12642413), nucleic acid encoding a chimpanzee NIS polypeptide of the nucleic acid sequence set forth in GenBank® Accession No. XM_524154 (GI No. 114676080), nucleic acid encoding a dog NIS polypeptide of the nucleic acid sequence set forth in GenBank® Accession No. XM_541946 (GI No. 73986161), nucleic acid encoding a cow NIS polypeptide of the nucleic acid sequence set forth in GenBank® Accession No. XM_581578 (GI No. 297466916), nucleic acid encoding a pig NIS polypeptide of the nucleic acid sequence set forth in GenBank® Accession No. NM 214410 (GI No. 47523871), and nucleic acid encoding a rat NIS polypeptide of the nucleic acid sequence set forth in GenBank® Accession No. NM_052983 (GI No. 158138504).

Nucleic acid inserted into the genome of a vesicular stomatitis virus (e.g., nucleic acid encoding a NIS polypeptide and/or nucleic acid encoding an IFN polypeptide) can be flanked by viral intragenic regions containing the gene transcription start and stop codes required for transcription of the inserted nucleic acid sequences by the viral polymerase. Examples of such viral intragenic regions include, without limitation, those set forth in FIG. 10.

The nucleic acid sequences of a vesicular stomatitis virus provided herein that encode a VSV N polypeptide, a VSV P polypeptide, a VSV M polypeptide, a VSV G polypeptide, and a VSV L polypeptide can be from a VSV Indiana strain as set forth in GenBank® Accession Nos. NC_001560 (GI No. 9627229) or can be from a VSV New Jersey strain.

In one aspect, this document provides vesicular stomatitis viruses containing a nucleic acid molecule (e.g., an RNA molecule) having, in a 3' to 5' direction, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding an IFN polypeptide, a nucleic acid sequence that is a template for a positive sense transcript encoding a VSV G polypeptide, a nucleic acid sequence that is a template for a positive sense transcript encoding a NIS polypeptide, and a nucleic acid sequence that is a template for a positive sense transcript encoding a VSV L polypeptide. Such vesicular stomatitis viruses can infect cells (e.g., cancer cells) and direct the expression of the IFN polypeptide and the NIS polypeptide by the infected cells.

Any appropriate method can be used to insert nucleic acid (e.g., nucleic acid encoding an IFN polypeptide and/or nucleic acid encoding a NIS polypeptide) into the genome of a vesicular stomatitis virus. For example, the methods described elsewhere (Obuchi et al., *J. Virol.,* 77(16):8843-56 (2003)); Goel et al., *Blood,* 110(7):2342-50 (2007)); and Kelly et al., *J. Virol.,* 84(3):1550-62 (2010)) can be used to insert nucleic acid into the genome of a vesicular stomatitis virus. Any appropriate method can be used to identify vesicular stomatitis viruses containing a nucleic acid molecule described herein. Such methods include, without limitation, PCR and nucleic acid hybridization techniques such as Northern and Southern analysis. In some cases, immunohistochemistry and biochemical techniques can be used to determine if a vesicular stomatitis virus contains a particular nucleic acid molecule by detecting the expression of a polypeptide encoded by that particular nucleic acid molecule.

In another aspect, this document provides nucleic acid molecules that encode a VSV N polypeptide, a VSV P polypeptide, a VSV M polypeptide, an IFN polypeptide, a VSV G polypeptide, a NIS polypeptide, and a VSV L polypeptide. For example, a nucleic acid molecule provided herein can be a single nucleic acid molecule that includes a nucleic acid sequence that encodes a VSV N polypeptide, a nucleic acid sequence that encodes a VSV P polypeptide, a nucleic acid sequence that encodes a VSV M polypeptide, a nucleic acid sequence that encodes an IFN polypeptide, a nucleic acid sequence that encodes a VSV G polypeptide, a nucleic acid sequence that encodes a NIS polypeptide, and a nucleic acid sequence that encodes a VSV L polypeptide.

The term "nucleic acid" as used herein encompasses both RNA (e.g., viral RNA) and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

This document also provides method for treating cancer (e.g., to reduce tumor size, inhibit tumor growth, or reduce the number of viable tumor cells). For example, a vesicular stomatitis virus provided herein can be administered to a mammal having cancer to reduce tumor size, to inhibit cancer cell or tumor growth, and/or to reduce the number of viable cancer cells within the mammal. A vesicular stomatitis virus provided herein can be propagated in host cells in order to increase the available number of copies of that virus, typically by at least 2-fold (e.g., by 5- to 10-fold, by 50- to 100-fold, by 500- to 1,000-fold, or even by as much as 5,000- to 10,000-fold). In some cases, a vesicular stomatitis virus provided herein can be expanded until a desired concentration is obtained in standard cell culture media (e.g., DMEM or RPMI-1640 supplemented with 5-10% fetal bovine serum at 37° C. in 5% $CO_2$). A viral titer typically is assayed by inoculating cells (e.g., BHK-21 cells) in culture.

Vesicular stomatitis viruses provided herein can be administered to a cancer patient by, for example, direct injection into a group of cancer cells (e.g., a tumor) or intravenous delivery to cancer cells. A vesicular stomatitis virus provided herein can be used to treat different types of cancer including, without limitation, myeloma (e.g., multiple myeloma), melanoma, glioma, lymphoma, mesothelioma, and cancers of the lung, brain, stomach, colon, rectum, kidney, prostate, ovary, breast, pancreas, liver, and head and neck.

Vesicular stomatitis viruses provided herein can be administered to a patient in a biologically compatible solution or a pharmaceutically acceptable delivery vehicle, by administration either directly into a group of cancer cells (e.g., intratumorally) or systemically (e.g., intravenously). Suitable pharmaceutical formulations depend in part upon the use and the route of entry, e.g., transdermal or by injection. Such forms should not prevent the composition or formulation from reaching a target cell (i.e., a cell to which the virus is desired to be delivered to) or from exerting its effect. For example, pharmacological compositions injected into the blood stream should be soluble.

While dosages administered will vary from patient to patient (e.g., depending upon the size of a tumor), an effective dose can be determined by setting as a lower limit the concentration of virus proven to be safe and escalating to higher doses of up to $10^{12}$ pfu, while monitoring for a reduction in cancer cell growth along with the presence of any deleterious side effects. A therapeutically effective dose typically provides at least a 10% reduction in the number of cancer cells or in tumor size. Escalating dose studies can be used to obtain a desired effect for a given viral treatment (see, e.g., Nies and Spielberg, "Principles of Therapeutics," In Goodman & Gilman's *The Pharmacological Basis of Therapeutics*, eds. Hardman, et al., McGraw-Hill, NY, 1996, pp 43-62).

Vesicular stomatitis viruses provided herein can be delivered in a dose ranging from, for example, about $10^3$ pfu to about $10^{12}$ pfu (e.g., about $10^5$ pfu to about $10^{12}$ pfu, about $10^6$ pfu to about $10^{11}$ pfu, or about $10^6$ pfu to about $10^{10}$ pfu). A therapeutically effective dose can be provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses can be administered by the same route as initially used or by another route. A therapeutically effective dose can be delivered in several discrete doses (e.g., days or weeks apart) and in one embodiment, one to about twelve doses are provided. Alternatively, a therapeutically effective dose of vesicular stomatitis viruses provided herein can be delivered by a sustained release formulation. In some cases, a vesicular stomatitis virus provided herein can be delivered in combination with pharmacological agents that facilitate viral replication and spread within cancer cells or agents that protect non-cancer cells from viral toxicity. Examples of such agents are described elsewhere (Alvarez-Breckenridge et al., *Chem. Rev.,* 109(7):3125-40 (2009)).

Vesicular stomatitis viruses provided herein can be administered using a device for providing sustained release. A formulation for sustained release of vesicular stomatitis viruses can include, for example, a polymeric excipient (e.g., a swellable or non-swellable gel, or collagen). A therapeutically effective dose of vesicular stomatitis viruses can be provided within a polymeric excipient, wherein the excipient/virus composition is implanted at a site of cancer cells (e.g., in proximity to or within a tumor). The action of body fluids gradually dissolves the excipient and continuously releases the effective dose of virus over a period of time. Alternatively, a sustained release device can contain a series of alternating active and spacer layers. Each active layer of such a device typically contains a dose of virus embedded in excipient, while each spacer layer contains only excipient or low concentrations of virus (i.e., lower than the effective dose). As each successive layer of the device dissolves, pulsed doses of virus are delivered. The size/formulation of the spacer layers determines the time interval between doses and is optimized according to the therapeutic regimen being used.

Vesicular stomatitis viruses provided herein can be directly administered. For example, a virus can be injected directly into a tumor (e.g., a breast cancer tumor) that is palpable through the skin. Ultrasound guidance also can be used in such a method.

Alternatively, direct administration of a virus can be achieved via a catheter line or other medical access device, and can be used in conjunction with an imaging system to localize a group of cancer cells. By this method, an implantable dosing device typically is placed in proximity to a group of cancer cells using a guidewire inserted into the medical access device. An effective dose of a vesicular stomatitis virus provided herein can be directly administered to a group of cancer cells that is visible in an exposed surgical field.

In some cases, vesicular stomatitis viruses provided herein can be delivered systemically. For example, systemic delivery can be achieved intravenously via injection or via an intravenous delivery device designed for administration of multiple doses of a medicament. Such devices include, but are not limited to, winged infusion needles, peripheral intravenous catheters, midline catheters, peripherally inserted central catheters, and surgically placed catheters or ports.

The course of therapy with a vesicular stomatitis virus provided herein can be monitored by evaluating changes in clinical symptoms or by direct monitoring of the number of cancer cells or size of a tumor. For a solid tumor, the effectiveness of virus treatment can be assessed by measuring the size or weight of the tumor before and after treatment. Tumor size can be measured either directly (e.g., using calipers), or by using imaging techniques (e.g., X-ray, magnetic resonance imaging, or computerized tomography) or from the assessment of non-imaging optical data (e.g., spectral data). For a group of cancer cells (e.g., leukemia cells), the effectiveness of viral treatment can be determined by measuring the absolute number of leukemia cells in the circulation of a patient before and after treatment. The effectiveness of viral treatment also can be assessed by monitoring the levels of a cancer specific antigen. Cancer specific antigens include, for example, carcinoembryonic antigen (CEA), prostate specific antigen (PSA), prostatic acid phosphatase (PAP), CA 125, alpha-fetoprotein (AFP), carbohydrate antigen 15-3, and carbohydrate antigen 19-4.

The invention will be further described in the following examples, which do not limit the scope of the invention described in the claims.

EXAMPLES

Example 1—Single Dose Intravenous Virotherapy Using Vesicular Stomatitis Viruses that Express an IFN Polypeptide and/or a NIS Polypeptide Mediates Oncolytic Tumor Debulking and Immunotherapeutic Eradication of Residual Disease Vesicular stomatitis viruses designed to express a mouse IFN beta polypeptide (VSV-mIFN) and vesicular stomatitis viruses designed to express both a mouse IFN beta polypeptide and a human NIS polypeptide (VSV-mIFN-NIS; FIG. 1A) were created using methods similar to those described elsewhere (Obuchi et al., *J. Virol.,* 77(16):8843-56 (2003)); Goel et al., *Blood,* 110(7):2342-50 (2007)); Kelly et al., *J. Virol.,* 84(3):1550-62 (2010); and Lawson et al., *Proc. Nat'l. Acad. Sci. USA,* 92(10):4477-81 (1995) Erratum in: *Proc. Nat'l. Acad. Sci. USA,* 92(19):9009 (1995)). Likewise, vesicular stomatitis viruses designed to express a human IFN beta polypeptide and a human NIS polypeptide (VSV-hIFN-NIS; FIG. 1A) were created. Briefly, nucleic acid sequences of desired transgenes were generated with specific restriction sites using PCR. The transgenes were inserted at specific insertion sites into a plasmid encoding the positive strand of the VSV genome in a 5' to 3' orientation. The modified plasmid was expanded and infective virus was recovered by infection with vaccinia virus coding for required T7 polymerase and transfection of VSV viral proteins N, P, and L. This allowed production of required viral polypeptides allowing generation of the negative sense viral genome that was assembled into infective virions. Recovered virus was amplified, and infective dose was measured on an appropriate cell line in culture (e.g., BHK-21 cells). The nucleic acid sequence of the mouse IFN beta polypeptide used to make these vesicular stomatitis viruses is set forth in GenBank® Accession No. NM_010510.1 (GI No. 6754303). The nucleic acid sequence of the human IFN beta polypeptide used to make these vesicular stomatitis viruses is set forth in GenBank® Accession No. NM_002176.2 (GI No. 50593016). The nucleic acid sequence of the human NIS polypeptide used to make these vesicular stomatitis viruses is set forth in GenBank® Accession No. NM_000453.2 (GI No. 164663746).

When nucleic acid encoding the human NIS polypeptide was inserted upstream of the nucleic acid encoding the VSV G polypeptide, functional virions were not generated because the NIS expression levels appear to have been too high for cells to remain viable and allow viral propagation. Inserting nucleic acid encoding the NIS polypeptide downstream of the nucleic acid encoding the VSV G polypeptide resulted in the generation of functional NIS-expressing virions due to lower quantities of NIS polypeptide being produced thereby allowing not only efficient viral propagation, but also sufficient quantities of NIS polypeptide for functional iodide uptake in infected cells (FIG. 2B).

Figure 2A:
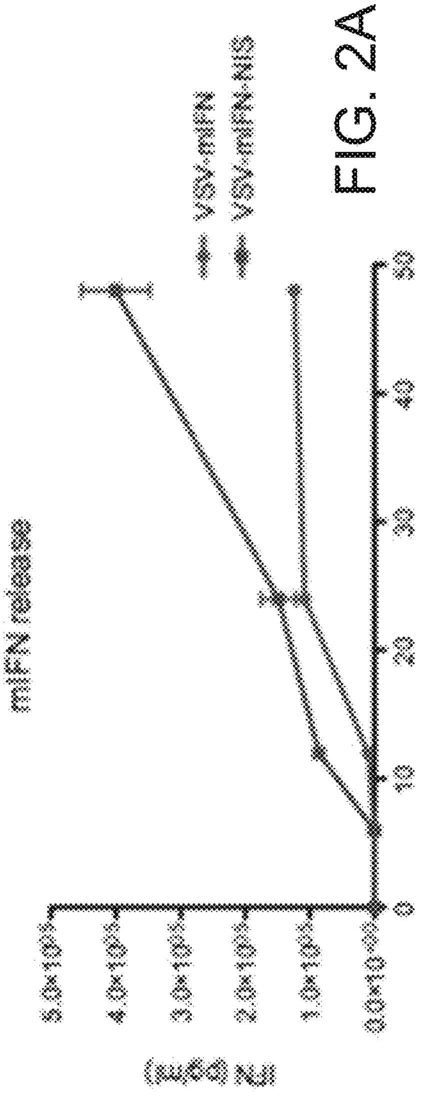
FIGS. 2A and 2B.
Figure 2B:
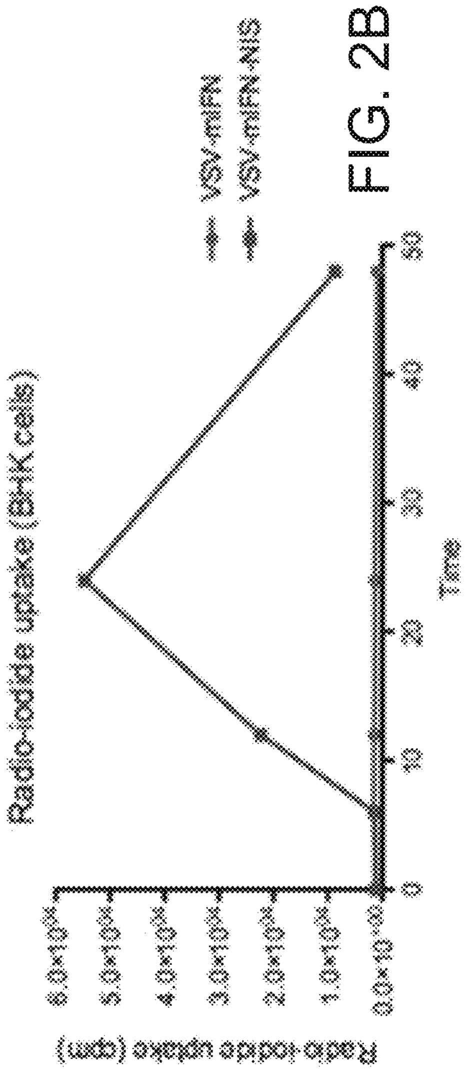

Inserting nucleic acid encoding an IFN polypeptide between the nucleic acid encoding the VSV M polypeptide and the nucleic acid encoding the VSV G polypeptide resulted in viruses that infected cells and produced a significantly increased level of IFN polypeptide expression that was observed in the supernatant from infected cells (FIG. 2A). The VSV-IFN-NIS viruses were able to replicate efficiently in vitro in infected cells and also express high levels of functional NIS as shown by the ability of the infected cells to take up radio-iodide (FIG. 2B).

Purified stocks of the two VSV-IFN-NIS viruses were titrated on BHK (hamster) cells (FIG. 1B), and cell supernatants were harvested to confirm the secretion of virally encoded IFNβ. High concentrations of human or murine IFNβ were detected in supernatants of BHK cells infected with VSV-hIFN-NIS and VSV-mIFN-NIS, respectively (FIG. 1D), and radioiodine uptake studies confirmed perchlorate sensitive (i.e., NIS-mediated) concentration of radioactive iodine in virus-infected cells (FIG. 1C), maximal at 24 hours after high multiplicity infection.

To evaluate the in vivo activity of the VSV-IFN-NIS viruses, the 5TGM1 and MPC-11 murine myeloma cell lines were chosen because they reliably form subcutaneous or orthotopic tumors in immunocompetent syngeneic mice (Lichty et al., *Hum. Gene Ther.,* 15:821-831 (2004) and Turner et al., *Human Gene Therapy,* 9:1121-1130 (1998)). Both lines were confirmed susceptible to VSV-IFN-NIS infection (FIG. 1E), resulting in functional NIS expression, IFNβ release, and subsequent cell killing. To determine whether intravenously administered VSV-IFN-NIS viruses could extravasate from tumor blood vessels and spread through the parenchyma of the tumor, subcutaneous 5TGM1 or MPC-11 tumors were grown (~5 mm diameter) in syngeneic mice, a single intravenous dose of $10^8$ $TCID_{50}$ VSV-IFN-NIS virus was administered, and the biodistribution of virally encoded NIS expression was noninvasively monitored by daily SPECT/CT imaging using 99mTcO4 (6 hour half-life) as tracer (FIG. 3A). These tracer uptake studies indicated that the virus was efficiently extravasating from tumor blood vessels and suggested that it may be rapidly spreading in the subcutaneous tumors.

To confirm that the virus was actually replicating and spreading in the tumor parenchyma, selected tumors were harvested immediately after SPECT/CT imaging at 24, 48, and 72 hours post VSV-IFN-NIS virus administration and subjected to (i) autoradiography to detect viable NIS-expressing tumor cells; (ii) immunofluorescence (IF) to detect VSV antigens, and (iii) TUNEL staining to identify dead or dying cells.

Careful analysis of the data shown in FIG. 3B indicated the existence of large, approximately spherical zones of VSV infection in which the tumor cells at the center were apoptotic and those at the periphery remained viable (see also FIG. 8), express NIS (FIG. 5), and concentrate 99mTcO4 (FIG. 9). Quantitative analysis of IF and TUNEL data indicated a significant increase in the number of virus-infected and apoptotic cells between 24 and 48 hours post virus administration (FIG. 3C). By 72 hours after infection, the growing zones of VSV infection largely coalesced, resulting in wholesale tumor destruction (FIG. 3B and FIG. 8).

Figure 4A:
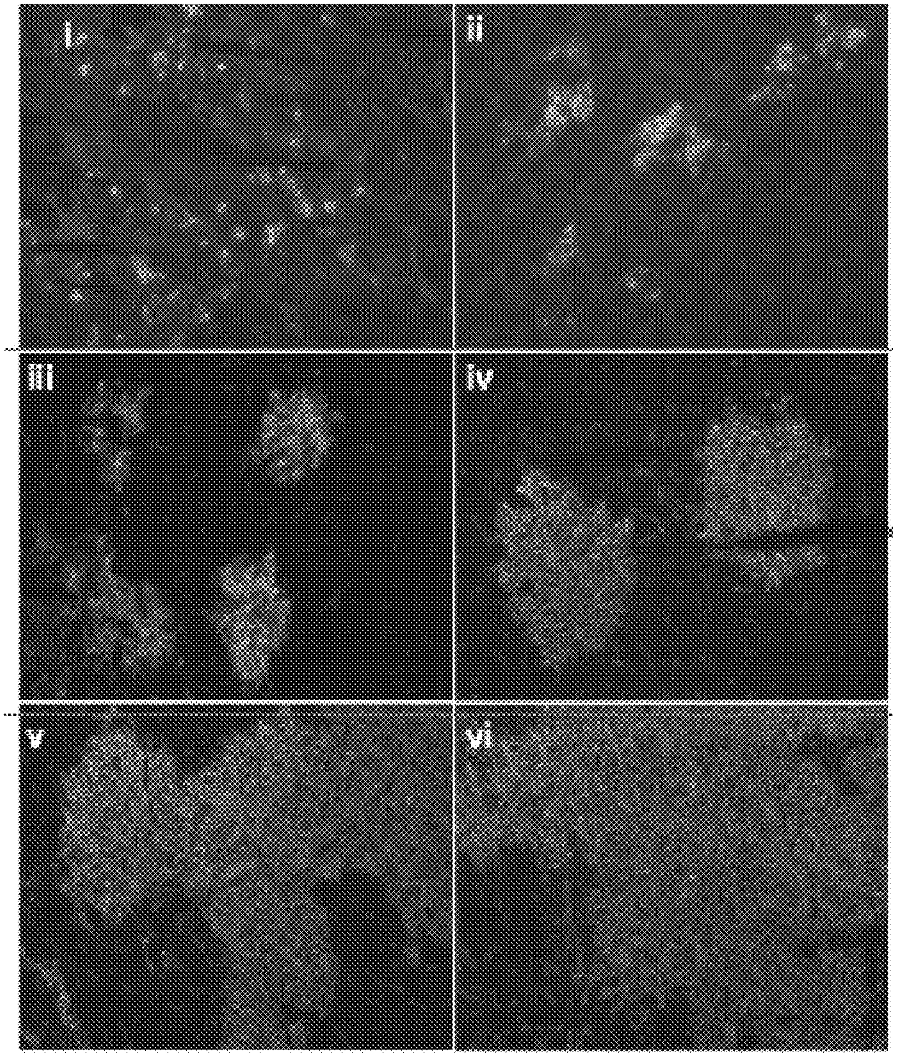

Additional experiments were conducted to characterize the kinetics of virus spread at very early time-points, during the first 24 hours after virus administration (FIG. 4A). Analysis of tumor sections harvested 6 hours after IV virus administration and stained for both VSV and CD31-positive blood vessels revealed individual scattered VSV infected cells, mostly close to tumor blood vessels. By 12 hours, small clusters of virus infected cells were visible and by 18 hours they grew significantly until by 24 hours they exhibited the typical appearance described previously—apoptotic at the center and viable at the periphery. Analysis of these dual CD31NSV stained sections (FIG. 4A, panels i-vi) indicated that the endothelial cells lining tumor blood vessels did not succumb to VSV infection, even when completely surrounded by VSV-infected tumor cells, shown at high magnification in FIG. 4B. By plotting average diameters of infectious centers (measured as number of cells across) at 6, 12, 18, and 24 hour time-points (FIG. 4C), it appeared that the virus spread centrifugally at a constant rate, taking approximately 2 hours to infect each successive layer of cells in the expanding sphere. The rate of accrual of new cells into each infectious center therefore increased as the infection progressed, and it was estimated that each center contained approximately 10,000 cells by 24 hours after virus delivery.

Figure 4B:
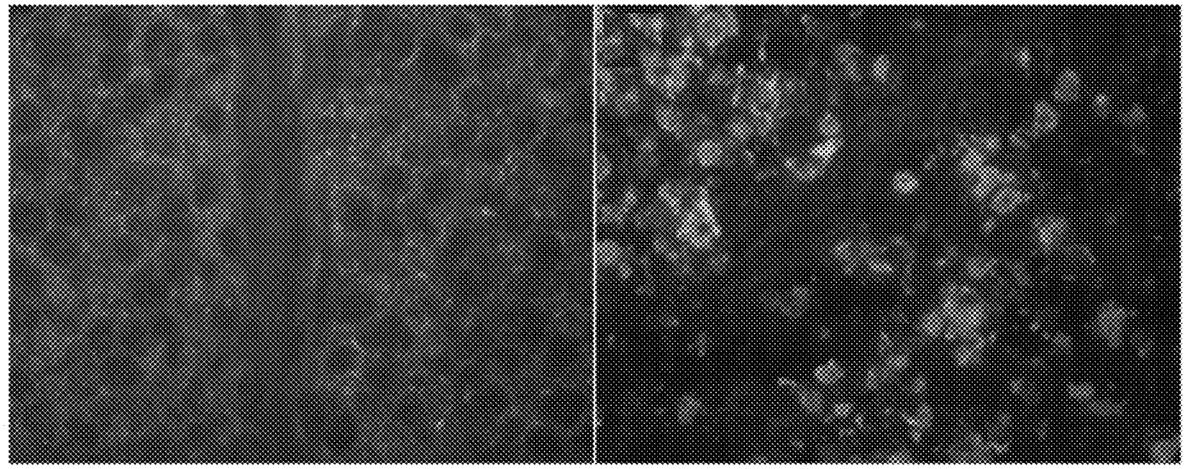
Figure 4C:
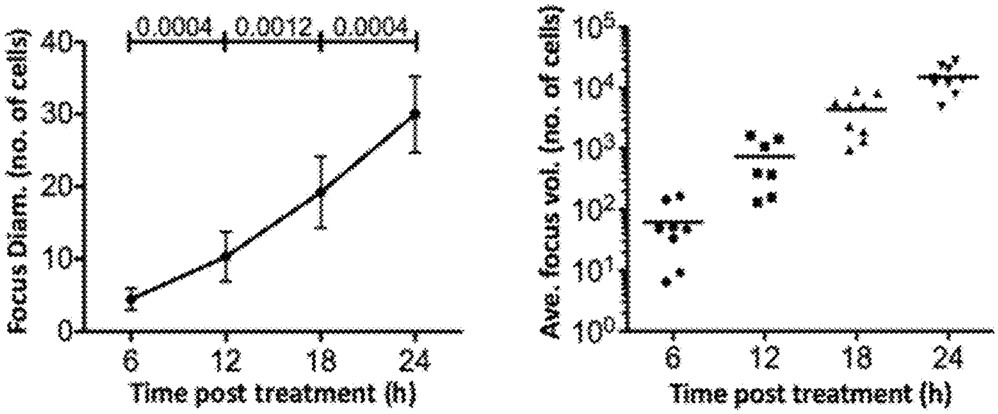
Figure 4D:
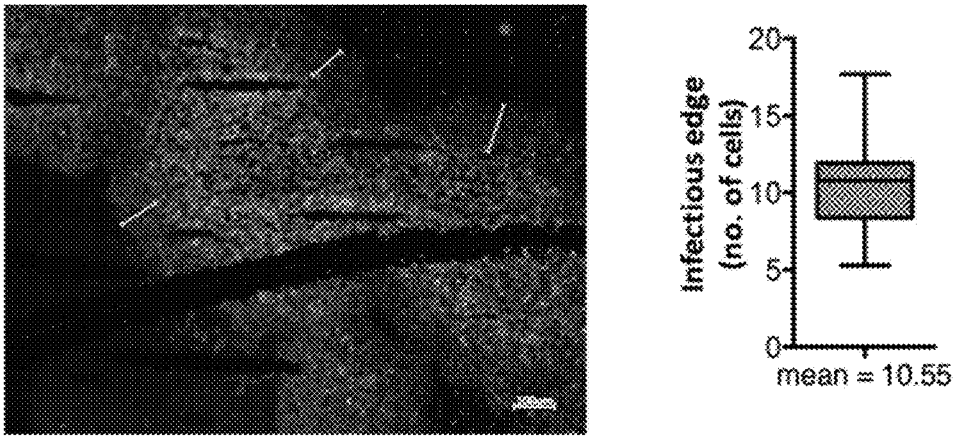

To determine the approximate time from infection to death of infected tumor cells in vivo, the average diameter of the rim of viable, VSV-infected (i.e. TUNEL-negative, VSV-positive) cells at the advancing edge of intratumoral infection was measured to be approximately 10 cells (FIG. 4D). Thus, the virus spread centrifugally, and it took approximately 2 hours to pass the virus on to an adjacent cell (FIG. 4C), while cell death did not occur until the rim of infected cells advanced by 10 cell diameters (FIG. 4D). Combining these observations, it was concluded that it takes approximately 20 hours for an infected cells to become apoptotic.

To determine whether efficient extravasation and rapid intratumoral spread of the virus is associated with tumor regression, additional groups of C57KaLwRij mice with subcutaneous 5TGM1 tumors were treated with a single intravenous dose of $10^8$ $TCID_{50}$ VSV-IFN-NIS and were followed longer term with daily health status checks and tumor measurements. Tumors regressed rapidly in the majority of VSV-mIFN-NIS and VSV-hIFN-NIS treated animals (FIG. 6A). Occasional very early deaths were not associated with neurotoxicity and were presumed due to rapid tumor lysis syndrome, although this was not formally proven. Interestingly, two to three weeks after administration of the viral therapy, tumor recurrence was seen in most of the animals treated with VSV-hIFN-NIS, but not in those treated with VSV-mIFN-NIS (FIGS. 6A and 6B), suggesting that the virally encoded mouse IFNβ, but not the human IFNβ, was capable of activating mechanisms that lead to the complete eradication of residual disease in this syngeneic immunocompetent mouse model. Retreatment of relapsing tumors with VSV-IFN-NIS was not attempted since all of the mice had by that time developed high titers of anti-VSV antibodies (FIG. 6C).

Figures 7A, 7B, 7C, 7D, 7E:
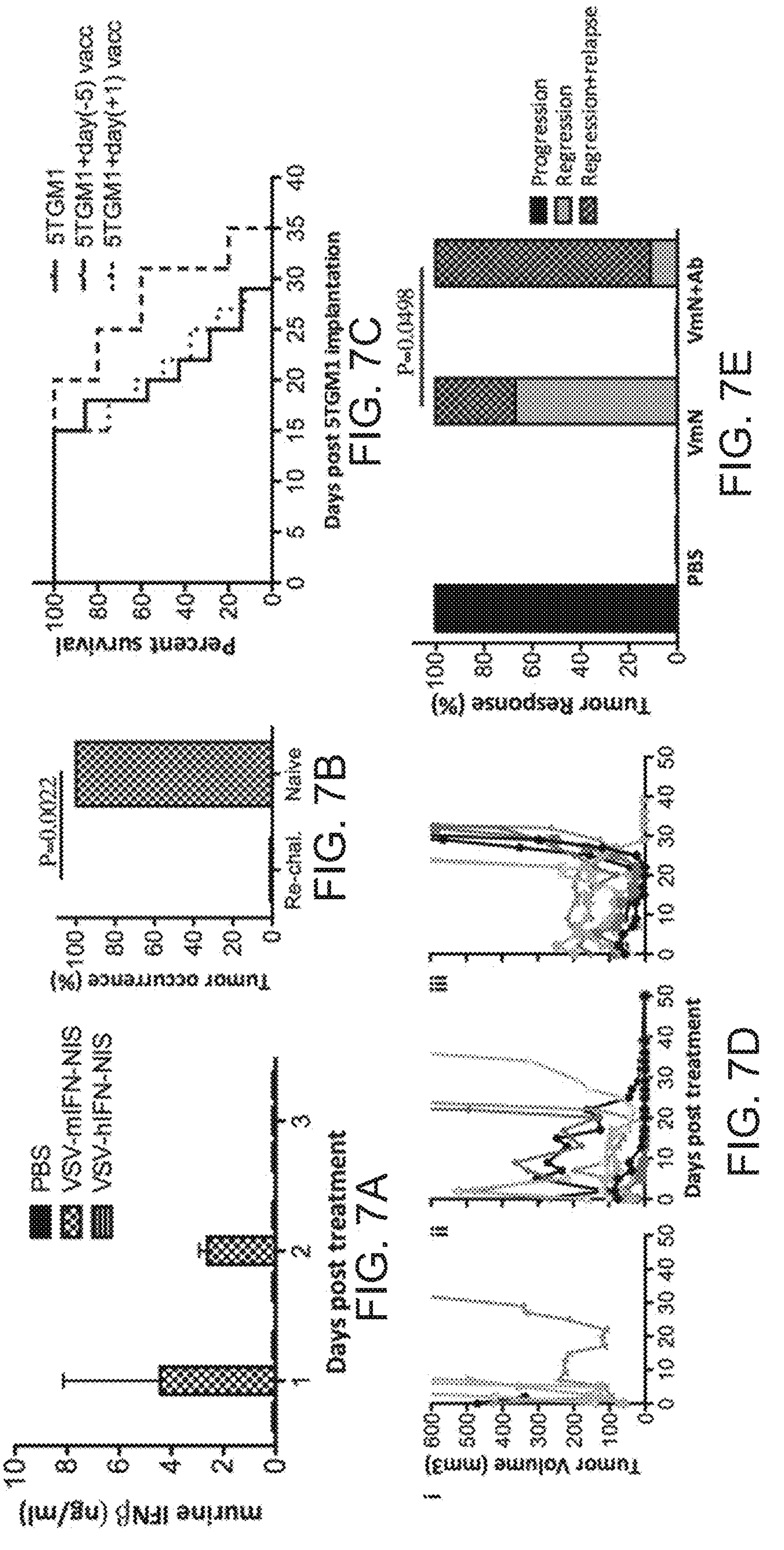

Measurement of serum IFNβ levels in virus treated animals indicated that this virally encoded cytokine was released into the bloodstream by virally infected tumor cells at early time-points after virus administration (FIG. 7A). Antitumor actions of interferon beta include the direct inhibition of tumor cell proliferation, natural killer cell activation, anti-angiogenesis, and the enhancement of antitumor T cell responses. However, proliferation of 5TGM1 and MPC11 myeloma cells in vitro was not adversely affected even at high concentrations of IFNβ (FIG. 1F). Moreover, analysis of CD31 or CD3 stained sections of virus treated tumors did not reveal any evidence for inhibition of anti-angiogenic activity, nor for tumor infiltration by host T lymphocytes (FIG. 4B). However, virus treated animals whose tumors did not recur were found to be resistant to re-challenge with 5TGM1 tumor cells (FIG. 7B), indicating that mice had developed 5TGM1 specific antitumor immunity. To determine whether syngeneic VSV-infected myeloma cells could provoke a specific anti-myeloma immune response, syngeneic mice were immunized with a single subcutaneous injection of $10^7$ VSV-infected 5TGM1 cells, either one day after or five days prior to subcutaneous tumor cell implantation. Tumor growth was delayed resulting in a significant enhancement of survival in mice that were immunized 5 days prior to tumor challenge (FIG. 7C), indicating that the VSV-infected tumor cells provoked a modest antitumor immune response. However, the VSV-infected tumor cell vaccine exhibited no detectable antitumor activity in mice bearing even small, established tumors, suggesting that antitumor immunity was effective only in the context of minimal disease burden.

To determine whether the lower tumor relapse rates in VSV-mIFN-NIS treated mice could be attributed to virally encoded IFNβ enhancing the antitumor T-cell response, a cocktail of anti-CD4 and anti-CD8 antibodies was used to deplete T-cells. Tumors responded equally well to the intravenous VSV-mIFN-NIS therapy regardless of T cell depletion status, but the rate of tumor recurrence was significantly higher in T-cell depleted mice (FIGS. 7D and 7E). These results indicate that eradication of residual tumor cells after oncolytic debulking by VSV-mIFN-NIS was mediated by tumor-specific T cells whose amplification was stimulated by the virally encoded mouse IFNβ.

When compared to the VSV-Δ51-NIS virus described in the Goel et al. reference (*Blood,* 110(7):2342-50 (2007)), which exhibited weak oncolytic efficacy in the immune competent 5TGM1 syngeneic multiple myeloma mouse model (C57Bl/KalwRijHsd), the VSV-IFN and VSV-IFN-NIS viruses exhibited greatly superior replication kinetics. In addition, compared to the VSV-Δ51-NIS virus, the VSV-IFN-NIS viruses induced higher NIS polypeptide expression in vitro. In vivo therapy studies demonstrated that a single intravenous dose of each of the VSV-IFN and VSV-IFN-NIS viruses promoted tumor regression and significantly prolonged survival of immunocompetent mice bearing subcutaneous or orthotopic 5TGM1 myeloma tumors. Tc-99m imaging studies conducted in mice treated with VSV-IFN-NIS viruses exhibited tumor specific viral NIS polypeptide expression and radio-isotope uptake that increased concurrently with intratumoral viral spread. Further, there were no indications of neurotoxicity following treatment with the VSV-IFN and VSV-IFN-NIS viruses. These results indicate that VSV-IFN-NIS viruses can be used as a therapeutic agent for cancer (e.g., multiple myeloma) that can be combined with radio-isotopes for both non-invasive imaging of viral biodistribution and radiovirotherapy.

The results provided herein demonstrate that vesicular stomatitis viruses encoding human IFNβ and human NIS exhibit oncolytic efficacy in vivo in an immune competent mouse model of multiple myeloma. Systemically administered virus was able to replicate in the tumor, express sufficient levels of functional NIS polypeptides, exert an oncolytic activity to induce tumor regression and improve survival, and exhibit superior NIS expression and oncolytic activity as compared to VSV Δ51-NIS virus.

Cell Culture and Viruses

Cell lines were cultured in media supplemented with 10% fetal bovine serum (FBS), 100 U/mL penicillin and 100 mg/mL streptomycin. BHK-21 and MPC-11 cells, obtained from American Type cell culture (ATCC), were grown in Dulbecco Modified eagles medium (DMEM). 5TGM1 cells were obtained from Dr. Babatunde Oyajobi (UT Health Sciences Center, San Antonio, TX) and grown in Iscove's modified Dulbecco medium (IMDM). B-16 murine melanoma cells were obtained from R. Vile and grown in DMEM. All cell lines tested negative for mycoplasma contamination.

Restriction sites were engineered into a pVSV-XN2 plasmid, containing the VSV positive strand antigenome, at the M/G and the G/L gene junctions preceded by the putative VSV intergenic sequence (TATG(A)$_7$CTAACAG) required for functional transgene expression (Schnell et al., *J. Virol.,* 70:2318-2323 (1996)). Restriction site flanked cDNA coding for murine IFNβ, human IFNβ, and NIS genes were generated by PCR. Murine or human IFNβ were incorporated into a single NotI site (M/G junction), while NIS was incorporated into XhoI and NheI sites (G/L junction) to generate VSV-IFN-NIS plasmid. VSV-IFN-NIS virus was rescued using methods described elsewhere (Whelan et al., *Proc. Natl. Acad. Sci. USA,* 92:8388-8392 (1995)). Viruses were subsequently amplified in BHK-21 cells, purified by filtration of cell supernatant, and pelleted by centrifugation through 10% w/v sucrose. Viral titer was measured in BHK-21 cells following infection using serially diluted virus stock to measure Tissue culture infective dose ($TCID_{50}$) determined using the Spearman and Karber equation.

In Vitro Viral Characterization

Viral titer was measured in supernatant following infection of BHK-21 cells (MOI 1.0, 1 hour at 37° C.). To measure in vitro radio-iodide uptake, cells were incubated in Hanks buffered salt solution (HBSS) with 10 mM HEPES (N-2-hydroxyethylpiperazine-N'-2-ethanesulfonic acid, pH 7.3) in the presence of radio-labeled NaI ($I^{125}$ at $1\times10^5$ cpm) +/−100 μM potassium perchlorate ($KClO_4$). IFNβ secretion in supernatant of infected cells was determined using an enzyme-linked immuno adsorbent assay (ELISA) against murine or human IFNβ (PBL Interferonsource). To compare IFN responsiveness, cells were pre-incubated with 100 U/mL murine IFNβ for 12 hours, followed by infection with VSV-GFP. Proliferation of viable cells was assessed by MTT assay (ATCC). Killing of 5TGM1 and MPC-11 by VSV-IFN-NIS (MOI 1.0) was similarly monitored at specific time points following infection by MTT assay shown as a percentage of untreated cells.

In Vivo Studies $5\times10^6$ 5TGM1 or MPC-11 murine myeloma cells were subcutaneously implanted on the right flank of 6-10 week-old syngeneic female C57B16/KaLwRij (Harlan, Netherlands) or Balb/c mice (Taconic), respectively. Tumor burden was measured by serial caliper measurements. Mice were administered with a single, intravenous dose of $1\times10^8$/0.1 mL VSV-IFN-NIS or equal volume PBS by tail vein injection. SPECT-CT imaging was carried out following intraperitoneal (IP) administration of 0.5 mCi Tc-99m and quantified as described elsewhere (Penheiter et al., *AJR Am. J. Roentgenol.,* 195:341-349 (2010)).

High Resolution Tumor Analysis

Tumors harvested at 24 hour intervals were frozen in OCT for sectioning. Tumor sections were analyzed by autoradiography and immunofluorescence (IF) for (i) VSV antigens using polyclonal rabbit anti-VSV generated in-house in the viral vector production labs at the Mayo Clinic, followed by Alexa-labeled anti-rabbit IgG secondary antibody (Invitrogen, Molecular Probes), (ii) cell death by TUNEL staining (DeadEnd™ Fluorometric TUNEL kit, Promega), and (iii) cellular nuclei using Hoescht 33342 (Invitrogen). Image quantification was performed on four random images from n=3 VSV-mIFN-NIS treated tumors (except n=2 tumors at 72 hours post treatment) using ImageJ software to obtain VSV or TUNEL(+) regions as percentage of tumor area. IF analysis of tumors harvested at 6 hour intervals detected VSV antigens and tumor blood vessels using a rat anti-mouse CD31 antibody (BD Pharmingen). Intratumoral foci size was quantified by measuring 7-8 foci from 2 tumors and dividing diameter by average tumor cell size (based on diameter measurements of 50 individual cells) to obtain foci diameter in numbers of cells. Volume of approximately spherical foci was estimated using formula, v=4/3(π*r3). Average width of rim of viable, VSV-infected cells was similarly quantified from IF images from n=3 tumors harvested at 48 hours post VSV-IFN-NIS administration.

Immune Studies in Immune Competent Mice

To measure generation of antiviral antibodies, serial 2-fold dilutions of heat-inactivated serum were pre-incubated with 500 $TCID_{50}$ VSV-GFP, and subsequently used to infect BHK-21 cells. Minimum serum dilution allowing VSV induced CPE was plotted. In vivo IFNβ secretion was measured in serum by ELISA. 5TGM1 vaccinations were administered by injecting $1\times10^7$ VSV-mIFN-NIS infected cells (MOI 10.0) subcutaneously in the left flank of syngeneic mice. T-cell depletion studies were performed in C57B16/KaLwRij mice by intraperitoneal administration of anti-CD4 and anti-CD8 antibodies (50 pg each) administered 3 times/week, followed by a weekly maintenance dose.

Statistical Methods

Visual displays of the data were used to assess for outliers or substantial departures from normality, and t-test was utilized where described. In all cases, two-tail P-values were provided which are not adjusted for multiple comparisons. Comparison of survival differences was performed using Log-rank test from Kaplan meier survival curves. For comparing tumor relapse rates in animal studies, the Fischer exact test was utilized due to small sample size.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating lung cancer, wherein said method comprises intravenously administering a composition comprising vesicular stomatitis viruses to a mammal comprising lung cancer cells at a dose from about $10^3$ pfu to about $10^{12}$ pfu, wherein said vesicular stomatitis viruses comprise an RNA molecule comprising, in a 3' to 5' direction, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding an IFN polypeptide, a nucleic acid sequence that is a template for a positive sense transcript encoding a VSV G polypeptide, a nucleic acid sequence that is a template for a positive sense transcript encoding a NIS polypeptide, and a nucleic acid sequence that is a template for a positive sense transcript encoding a VSV L polypeptide, wherein administration of said composition to said mammal is under conditions wherein said vesicular stomatitis viruses infect said cancer cells to form infected cancer cells, wherein said infected cancer cells express said IFN polypeptide and said NIS polypeptide, and wherein the number of cancer cells within said mammal is reduced following said administration.

2. The method of claim 1, wherein said mammal is a human.

3. The method of claim 1, wherein said IFN polypeptide is a human IFN beta polypeptide.

4. The method of claim 1, wherein said NIS polypeptide is a human NIS polypeptide.

* * * * *

SEQUENCE LISTING

```
Sequence total quantity: 1
SEQ ID NO: 1            moltype = DNA  length = 11
FEATURE                 Location/Qualifiers
misc_feature            1..11
                        note = poly (A) tract
source                  1..11
                        mol_type = other DNA
                        organism = synthetic construct
SEQUENCE: 1
tatgaaaaaa a                                                          11
```